United States Patent
Blume et al.

(10) Patent No.: US 6,916,921 B2
(45) Date of Patent: Jul. 12, 2005

(54) STEROID COMPOUNDS, USE OF THESE COMPOUNDS FOR THE PREPARATION OF MEIOSIS-REGULATING MEDICAMENTS AND METHOD FOR THE PREPARATION OF THESE COMPOUNDS

(75) Inventors: Thorsten Blume, Berlin (DE); Peter Esperling, Berlin (DE); Christa Hegele-Hartung, Mülheim/Ruhr (DE)

(73) Assignees: Schering AG, Berlin (DE); Novo Nordisk D/S, Bagsvaerd (DK)

( * ) Notice: Subject to any disclaimer, the term of this patent is extended or adjusted under 35 U.S.C. 154(b) by 90 days.

(21) Appl. No.: 10/105,939

(22) Filed: Mar. 26, 2002

(65) Prior Publication Data

US 2002/0188143 A1 Dec. 12, 2002

(30) Foreign Application Priority Data

Mar. 26, 2001 (EP) .............................. 01250108

(51) Int. Cl.$^7$ ................................ C07J 43/00

(52) U.S. Cl. ...................... 540/109; 540/107
(58) Field of Search ................. 514/176, 177, 514/182; 552/603, 554, 599; 540/107

(56) References Cited

U.S. PATENT DOCUMENTS

| | | | |
|---|---|---|---|
| 3,342,811 A | 9/1967 | Sarel et al. | |
| 3,419,661 A | 12/1968 | Elder | |
| 3,535,312 A | 10/1970 | Philippson | |

FOREIGN PATENT DOCUMENTS

| DE | 1930473 | 12/1970 |
|---|---|---|
| WO | 96/00235 | 1/1996 |
| WO | 96/27658 | 9/1996 |
| WO | 97/00884 | 1/1997 |
| WO | 98/28323 | 7/1998 |
| WO | WO 99/58549 | * 11/1999 |
| WO | 99/58549 | 11/1999 |
| WO | 99/61010 | 12/1999 |
| WO | 00/50065 | 8/2000 |
| WO | 00/50066 | 8/2000 |
| WO | 00/52142 | 9/2000 |
| WO | 01/19354 | 3/2001 |
| WO | 01/62260 | 8/2001 |

OTHER PUBLICATIONS

Mangla et al., "Sterol C–methyl Transferase from *Prototheca wickerhamii* Mechanism, Sterol Specificity and Inhibition." Bioorganic & Medicinal Chemistry, vol. 8, p. 925–936, 2000.*

XP–001023708, Sterol C–methyl Transferase from *Prototheca wickerhamii* Mechanism, Sterol Specificity and Inhibition, Anil T. Mangla et al., Department of Chemistry and Biochemistry, Texas Tech University, Lubbock, TX 79409 USA, pp. 926–936, 2000.

XP–002104638, Active Site–directed Inhibitors of Cytochrome P–450, Structural And Mechanistic Implications Of A Side Chain–Substituted Series Of Amino–Steroids, Joel J. Sheets et al., pp. 11446–11452, 1983.

XP–002175968, Inhibition of Cholesterol Side–Chain Cleavage. 4.$^1$ Synthesis of A or B Ring Modified Azacholesterols, Matthias C. Lu et al., Journal of Medicinal Chemistry, 1981, vol. 24, No. 9, pp. 1038–1042.

XP–002175969, Steroid Amines. Part V.$^1$ 20–Pyrrolidin–1–ylpregnane Derivatives, M. Davis et al., J.C.S. Perkin I, pp. 1420–1424, 1972.

XP–002175971, Inhibitors of Ergosterol Biosynthesis and Growth of the Trypanosomatid Protozoan Crithidia fasciculata, Mohammad D. Rahman et al., The Journal of Biological Chemistry, vol. 265, No. 9, Issue of Mar. 25, pp. 4989–4996, 1990.

XP–002175972, Steroid Amines. Fungicides Derived from $\Delta^5$–3β–Hydroxybisnorcholenic Acid (Fernholz Acid), Hershel L. Herzog et al., H.L. Herzog, C.C. Payne and E. B. Hershberg, vol. 77, pp. 5324–5327, 1955.

XP002216553—Abstract of Japan—Hikim, Amiya P. Sinha: "Effect of 22.25–diazacholesterol dihydrochloride on the spermatogenesis of a wild rat, Bandicota bengalensis", 1987.

XP002216554—Abstract of Japan—Counsell, R.E. et al.: "Inhibition of cholesterol side–chain cleavage by azacholesterols", 1971.

XP002216549—Abstract of Japan—Kohan F. et al: "Hypocholesterolemic agents, 9. C–20 Epimeric 22,25–diazacholesterols" J.Med. Chem. (1972), 15(11), 1129–31.

(Continued)

*Primary Examiner*—Barbara P. Badio
(74) *Attorney, Agent, or Firm*—Millen, White, Zelano & Branigan, P.C.

(57) ABSTRACT

The present invention relates to steroid compounds of general formula X, which may advantageously be employed to stimulate meiosis in human oocytes, the steroid being specifically characterized by amino nitrogen bonded to C$^{17}$ of the steroid skeleton via a spacer A.

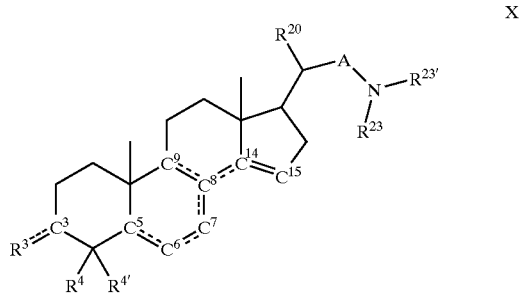

36 Claims, No Drawings

OTHER PUBLICATIONS

Figure 1B:
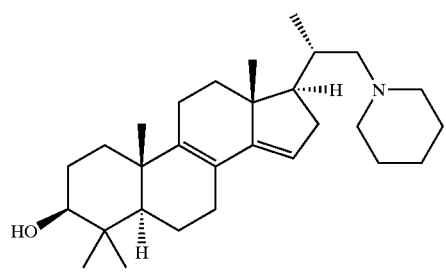
Figure 1B:
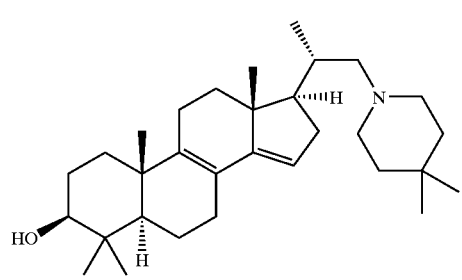
Figure 1B:
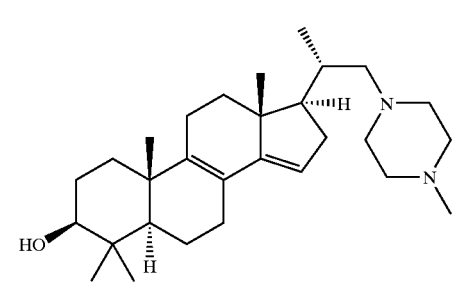
Figure 1B:
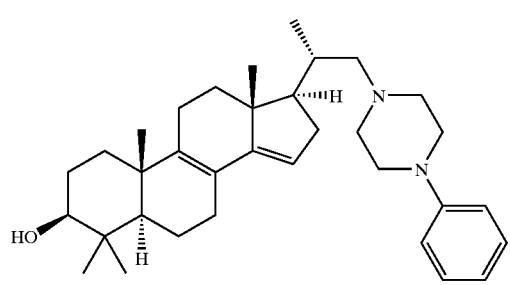
Figure 1B:
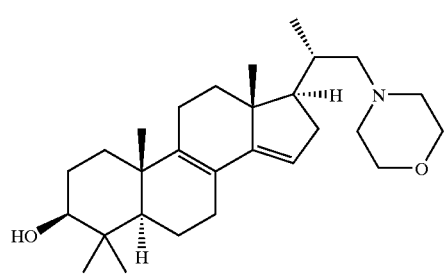

XP002216550—Abstract of Japan—Venton D.L. et al.: "Hypocholesterolemic agents. 10. Synthesis of some model azacholanic acids as potential regulators of steroid biosynthesis and metabolism" J. Med. Chem. (1973), 16(5), 571–3.

XP000982169—Abstract of Japan—Li J–S: "Synthesis And Evaluation Of Pregane Derivatives As Inhibitors Of Human Testicular 17Alpha–Hydroxylase/C17,20–Lyase" Journal of Medicinal Chemistry, American Chemical Society, Washington, U.S., vol. 39, No. 21, 1996, pag4es 4335–4339.

XP002216555—Abstract of Japan—Kabara, Jon J. et al.: "Structure–function activity of azasterols and nitrogen–containing steroids", 1976.

XP002216558—Abstract of Japan—Chen, Yihui et al.: "Synthesis of several analogs of antifungal steroid alkaloids", 1998.

XP002216551—Abstract of Japan—Rajeswari, SUndaramoorthi et al.: "A New Synthesis of amides from acyl fluorides and N–silylamines" Tetrahedron Lett. (1987), 28(43), 5099–102.

XP002216552—Abstract of Japan—Xie W et al.: "Structure–activity relationship of aza–steroids as PI–PLC inhibitors" Bioorganic & Medicinal Chemistry, England, May 2001, vol. 9, No. 5, (May 2001), pp. 1073–1083.

Amiya P. Sinha Hikim, "Effect of 22,25–diazacholesterol dihydrochloride on the spermatogenesis of a wild rat, Bandicota bengalensis," International Journal of Fertility, 1987, pp. 320–323, vol. 32, No. 4, CODEN:INJFA3, ISSN: 0020–725X, University of Calcutta, India, abstract only.

R. E. Counsell et al., "Inhibition of cholesterol side–chain cleavage by azacholesterols," Biochemical Pharmacology, 1971, pp. 2912–2915, vol. 20, No. 10, CODEN: BCPCA6, ISSN 0006–2952, The University of Michigan, Ann Arbor, MI, abstract only.

F. Kohen et al., "Hypocholesterolemic Agents. 9. C–20 Epimeric 22,25–Diazacholesterols," 1972, Journal of Medicinal Chemistry, pp. 1129–1131, vol. 15, No. 11, XP–002216549, The University of Michigan, Ann Arbor, MI.

D. L. Venton et al., "Hypocholesterolemic Agents. 10. Synthesis of some model Azacholanic Acids as potential regulators of steroid biosynthesis and metabolism," Journal of Medicinal Chemistry, 1973, pp. 571–573, vol. 16, No. 5, XP–002216550, The University of Michigan, Ann Arbor, MI.

* cited by examiner

STEROID COMPOUNDS, USE OF THESE COMPOUNDS FOR THE PREPARATION OF MEIOSIS-REGULATING MEDICAMENTS AND METHOD FOR THE PREPARATION OF THESE COMPOUNDS

The invention relates to pharmaceutically active steroid compounds, pharmaceutical compositions comprising these compounds, the use of these compounds for the preparation of a pharmaceutical composition being suitable to regulate reproduction, especially meiosis, of a contraceptive or as a profertility drug, a method for regulating reproduction, e.g. meiosis, a method for improving the possibility of an oocyte's ability to develop into a mammal as well as methods for the preparation of the novel steroid compounds.

Meiosis is the unique and ultimate event of germ cells, on which sexual reproduction is based. Meiosis comprises two meiotic divisions. During the first division, exchange between maternal and paternal genes take place before the pairs of chromosomes are separated into the daughter cells. These contain only half the number (1n) of chromosomes and 2c DNA. The second meiotic division proceeds without a DNA synthesis. This division therefore results in the formation of the haploid germ cells with only 1c DNA.

The meiotic events are similar in the male and female germ cells, but the time schedule and the differentiation processes, which lead to ova and to spermatozoa differ profoundly. All female germ cells enter the prophase of the first meiotic division early in life, often before birth, but all are arrested as oocytes later in the prophase (dictyate state) until ovulation after puberty. Thus, from early life the female has a stock of oocytes, which is drawn upon until the stock is exhausted. Meiosis in females is not completed until after fertilization, and results in only one ovum and two abortive polar bodies per germ cell. In contrast, only some of the male germ cells enter meiosis from puberty and leave population of germ cells throughout life. Once initiated, meiosis in the male cell proceeds without significant delay and produces four spermatozoa.

Only little is known about the mechanisms, which control the initiation of meiosis in the male and in the female. New studies indicate that follicular purines, hypoxanthine and adenosine could be responsible for meiotic arrest in the oocyte [S. M. Downs et al., *Dev. Biol.*, 82, 454–458 (1985); J. J. Epplg. et al., *Dev. Biol.*, 119, 313–321 (1986); S. M. Downs, *Mol. Reprod. Dev.*, 35, 82–94 (1993)]. The presence of a diffusible meiosis regulating substance was first described by Byskov et al. in a culture system of fetal mouse gonads [A. G. Byskov et al., *Dev. Biol.*, 52, 193–200 (1976)]. A meiosis activating substance (MAS) is secreted by the fetal mouse ovary, in which meiosis is ongoing, and a meiosis preventing substance (MPS) is released from the morphologically differentiated testis with resting, non-meiotic germ cells. It was suggested that the relative concentrations of MAS and MPS regulate the beginning, arrest and resumption of meiosis in the male and in the female germ cells [A. G. Byskov et al. in: *The Physiology of Reproduction* (eds. E. Knobil and J. D. Neill), Raven Press, New York (1994)]. Clearly, if meiosis can be regulated, reproduction can be controlled. In a recent article [A. G. Byskov et al., *Nature*, 374, 559–562 (1995)] the isolation of certain sterols is described that activate oocyte meiosis from bull testes and from human follicular fluid [T-MAS (testes meiosis-activating sterol) and FF-MAS (follicular fluid meiosis-activating sterol): 4,4-dimethyl-5α-cholesta-8,14, 24-trien-3β-ol].

It was also demonstrated that micromolar concentrations of synthetic FF-MAS are able to induce resumption of meiosis in a dose-dependent manner in rat oocytes that are arrested by the phosphodiesterase inhibitor IBMX (3-isobutyl-1-methyl xanthine) [C. Hegele-Hartung et al., *Biol. Reprod.*, 64, 418–424 (2001)]. It was shown that this effect can be observed when CEO (cumulus-enclosed oocytes) and DO (denuded oocytes) are cultured in vitro in the presence of FF-MAS.

Further substances that regulate the meiosis are described in WO 96/00235 A1, WO 96/27658 A1, WO 97/00884 A1, WO 98/28323 A1, WO 98/52965 A1, WO 99/58549 A1 and WO 00/68245 A1.

In WO 98/52965 A1 meiosis activating 20-aralkyl-5α-pregnane derivatives are described.

In WO 00/68245 A1 steroid compounds are disclosed, which are able to inhibit meiosis such that these compounds are useful as contraceptives in females and males. These compounds are primarily unsaturated cholestan derivatives characterized by a 3β-hydrogen atom bonded to the $C^{14}$ carbon atom of the cholestan skeleton.

In WO 96/00235 A1 meiosis inducing sterols, being known as intermediates in the biosynthesis of cholesterol, as well as certain structurally related synthetic sterols, are described. These substances have been found to regulate meiosis. Similar to cholesterol these sterols are provided with a side chain on $C^{17}$ in the sterol skeleton and further with at least one of a $\Delta^7$, $\Delta^8$ or $\Delta^{8(14)}$ double bond.

In WO 96/27658 A1 a method of stimulating meiosis of a germ cell is disclosed, which comprises administering to the cell in vivo, ex vivo or in vitro an effective amount of a compound, which causes accumulation of an endogenous meiosis activating substance to a level, at which meiosis is induced. Such compounds which cause accumulation of the meiosis activating substance are disclosed to be amphotericin B, aminoguanidine, 3β,5α,6β-trihydroxycholestane, melatonine, 6-chloromelatonine and 5-methoxytryptamine as well as other derivatives and agonists thereof. Meiosis activating substances are also reported to be inter alia 5α-cholestan-3β-ol, D-homo-cholesta-8,14-dien-3β-ol and 22,25-diazacholestrol, 25-aza-24,25-dihydrolanosterol, 24,25-lminolanosterol, 23- and 24-azacholestrol as well as 25-azacholestanol derivatives.

In WO 97/00884 A1 and in WO 98/28323 A1 substances are described which can be used for stimulating meiosis in vitro, in vivo or ex vivo. The compounds disclosed are hence agonists of naturally occurring meiosis activating substances and may therefore be used in the treatment of infertility which is due to insufficient stimulation of meiosis in females and males. In this document also some compounds are disclosed which may be antagonists of naturally occurring meiosis activating substances, such that these compounds may be suitable for use as contraceptives. The compounds disclosed inter alia comprise 5α-cholest-8-ene-3β-ols and 5α-cholest-8,14-dien-3β-ols which inter alia may be provided with an amino group in the side chain bonded to $C^{17}$ of the cholesterol skeleton, the amino group being bonded to the sterol skeleton via a $C_4$-spacer. To the amino group $C_1$–$C_4$ alkyl or $C_3$–$C_6$ cycloalkyl are bonded.

Further in WO 99/58549 A1 sterol derivatives are disclosed which are effective in regulating meiosis. These compounds are described to have the ability to relieve infertility in females and males, particularly in humans. The sterol derivatives being effective as regulating substances are inter alia (20R)-20-methyl-23-dimethylamino-5α-pregna-8,14-dien-3β-ol, (20R)-20-methyl-23-dimethylamino-5α-pregna-5,7-dien-3β-ol, 4,4-dimethyl-24-phenylamino-5α-chola-8,14-dien-3β-ol, 4,4-dimethyl-24-(N,N-dimethylamino)-24-cyano-5α-cholesta-8,14-dien-3β- ol and further a variety of 24-oic acid amides of sterols having one or more double bonds in the sterol skeleton.

Unsaturated sterol derivatives having an amino group in the side chain at $C^{17}$ have also been described by: J. J. Sheets and L. E. Vickery in: "Active Site-directed Inhibitors of Cytochrome P-450scc" in J. Biol. Chem., Vol.258 (19), 1983, pages 11446–11452 with regard to the effect of these sterols on bovine adenocortical cholesterol side chain cleavage cytochrome P-450 (P-450 scc). In this document inter alia 22-amino-23,24-bisnor-chol-5-en-3β-ol and 23-amino-24-norchol-5-en-3β-ol are disclosed.

Further unsaturated derivatives having an amino group in the side chain at $C^{17}$ have been reported by: A. T. Mangla and W. D. Nes in: "Sterol C-methyl Transferase from *Prototheca wickerhamii*, Mechanism, Sterol Specificity and Inhibition" in Bioorg. and Med. Chem. (2000), 8 (5), 925–936. In this document inter alia 23-aza-zymosterol is disclosed.

It has been discovered, when using previously described meiosis regulating components, that resumption of meiosis occurs in naked oocytes in vitro. However, these compounds were only marginal effective when stimulating meiosis in oocytes surrounded by granulosa cells (CEO=cumulus enclosed oocytes). The disclosure of the above documents is incorporated by reference.

One object of the present invention is to find substances that are useful for regulating reproduction, in particular meiosis, in females and males, especially in mammals and more specifically in humans.

It is another object of the present invention to provide a novel pharmaceutical composition comprising the novel substances.

It is another preferred object of the present invention to provide a use of the novel substances for the preparation of a pharmaceutical composition be suitable to regulate reproduction, especially meiosis.

It is another preferred object of the present invention to provide a novel method of regulating reproduction, e.g. meiosis.

It is a further object of the present invention to provide a method to treat human fertility.

It is a further object of the present invention to improve maturation of human oocytes.

It is still another object of the present invention to improve synchrony of nuclear, cytoplasmic and/or membranous oocyte maturation.

It is still another object of the present invention to improve fertility of oocytes.

It is still another object of the present invention to improve the rate of implantation of oocytes by human in vitro maturation and fertilization.

It is still a further object of the present invention to diminish the incidence of human preembryos with chromosome abnormalities (aneuploidy).

It is still a further object of the present invention to improve the cleavage rate of human preembryos.

It is still a further object of the present invention to improve the quality of human preembryos.

It is another object of the present invention to provide a method for the preparation of the novel substances.

According to the present invention steroid compounds of general formula X may advantageously be employed in regulating the reproduction, e.g. meiosis, in mammals, e.g. females and males, and in particular in humans:

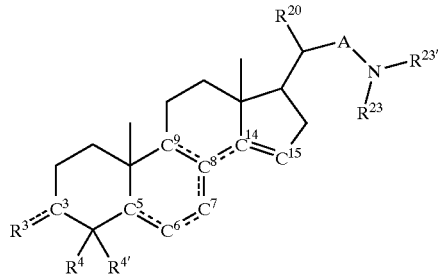

X wherein in the moiety

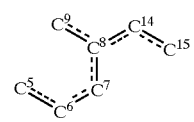

XA each bond between $C^5$ and $C^6$, between $C^6$ and $C^7$, between $C^7$ and $C^8$, between $C^8$ and $C^9$, between $C^8$ and $C^{14}$ and between $C^{14}$ and $C^{15}$, independently, is a single bond or a double bond, at least one of these bonds being a double bond, and wherein each carbon atom $C^5$, $C^6$, $C^7$, $C^8$, $C^9$, $C^{14}$ and $C^{15}$ is bonded to each neighbouring C atom by a single bond or at the most by one double bond, and wherein between all other carbon atoms of the steroid skeleton are single bonds, and $C^3R^3$ is a) $C^3$=O or b) $C^3H$—$OR^{3'}$, wherein $R^{3'}$ is selected from the group, comprising hydrogen, unsubstituted or substituted, linear or branched $C_1$–$C_{10}$ alkyl and $C^3(O)$—$R^{3''}$, bonded to the CH—O moiety via the C(O) moiety, wherein $R^{3''}$ is selected from the group, comprising
  i) substituted or unsubstituted, linear or branched $C_1$–$C_{10}$ alkyl,
  ii) substituted or unsubstituted, linear or branched $C_1$–$C_{10}$ fluoro alkyl,
  iii) unsubstituted or substituted $C_6$–$C_{10}$ aryl,
  iv) unsubstituted or substituted $C_5$–$C_{10}$ heteroaryl,
  v) unsubstituted or substituted, linear or branched $C_1$–$C_{10}$ alkyloxy and
  vi) unsubstituted or substituted, linear or branched $C_1$–$C_{10}$ alkylamino, or c) $C^3H$—$SO_2$—$R^{3'''}$ or $C^3$=$NOR^{3''}$, wherein $R^{3''}$ has the same meaning as above, or d) $C^3H$—O—$R^{3'''}$, wherein $R^{3'''}$ is unsubstituted or substituted, linear or branched $C_2$–$C_{10}$ alkylen and forms a cyclic ether both with the C atom of the steroid skeleton and the O atom, or e) a cyclic ring structure with the $C^3$ atom, wherein $R^3$ is unsubstituted or substituted, linear or branched $C_2$–$C_{10}$ alkylen, or f) $C^3H$-Hal, wherein Hal is F, Cl, Br or I, and $R^4$, $R^{4'}$ and $R^{20}$, independently, are selected from the group, comprising hydrogen and unsubstituted or substituted, linear or branched $C_1$–$C_4$ alkyl,
and
$R^{23}$ and $R^{23'}$, independently, are selected from the group, comprising:
a) hydrogen,
b) unsubstituted or substituted, linear or branched $C_1$–$C_8$ alkyl,
c) unsubstituted or substituted, linear or branched $C_2$–$C_8$ alkenyl,
d) unsubstituted or substituted, linear or branched $C_1$–$C_8$ alkyl, at least one of the alkyl carbon atoms being substituted by any of O, N and S,
e) unsubstituted or substituted, linear or branched $C_2$–$C_8$ alkenyl, at least one of the alkenyl carbon atoms being substituted by any of O, N and S and
f) unsubstituted or substituted, linear or branched $C_6$–$C_{10}$ aryl,
or
$R^{23}$ and $R^{23'}$ together form
a) an unsubstituted or substituted, linear or branched $C_2$–$C_7$ alkylen, especially $C_5$–$C_7$, group or
b) an unsubstituted or substituted, linear or branched $C_2$–$C_7$ alkylen, especially $C_5$–$C_7$, group, wherein at least one of the alkylen carbon atoms is replaced by any of O, N and S,
and
A is a methylen or ethylen group, the group being unsubstituted or substituted methylen or ethylen; in a preferred embodiment of the present invention A is methylen or ethylen,
with the proviso that the following compounds are disclaimed: (20R)-20-methyl-23-dimethylamino-5α-pregna-8, 14-dien-3β-ol and (20R)-20-methyl-23-dimethylamino-5α-pregna-5,7-dien-3β-ol, 23-aza-zymosterol, 22-amino-23,24-bisnorchol-5-en-3β-ol, 23-amino-24-norchol-5-en-3β-ol.

Preferably the invention relates to steroid compounds in which at least one double bond is present in the steroid skeleton between carbon atoms $C^6$, $C^7$, $C^8$, $C^9$, $C^{14}$ and $C^{15}$, respectively. In one further preferred embodiment of the present invention a double bond may be present between $C^5$ and $C^6$ in addition to the at least one double bond between $C^6$, $C^7$, $C^8$, $C^9$, $C^{14}$ and $C^{15}$, respectively. It is especially preferred to have a steroid in which the double bonds are conjugated to each other if more than one double bond is present in the steroid skeleton.

All indications to $C_n$ alkyl, $C_n$ fluoroalkyl, $C_n$ alkyloxy, $C_n$ alkylamino, $C_n$ cycloalkyl, $C_n$ alkylen, $C_n$ alkenyl, $C_n$ aryl, $C_n$ heteroaryl and the like relate to radicals with n carbon atoms in the moiety, the number of n carbon atoms including all carbon atoms in side chains of e.g. branched radicals. Unless otherwise described herein, an alkyl, alkoxy, alkylen or acyl group has 1 to 10 carbon atoms including side chain carbon atoms if these groups are branched; an alkenyl or alkynyl group has 2 to 10 carbon atoms including side chain carbon atoms if these groups are branched; further a cycloalkyl has 4 to 7 carbon atoms; an aryl has 6 to 10 carbon atoms; and a heterocyclic ring or a heteroaryl have 6 to 10 ring atoms. Further aryl also represents alkylaryl; heteroaryl also represents alkylheteroaryl; and cycloalkyl also represents alkylcycloalkyl.

The novel steroid compounds have a number of chiral centers such that these compounds exist in several isomeric forms. All these isomeric forms are within the scope of the present invention unless otherwise described herein.

A steroid compound with the following general formula is preferred:

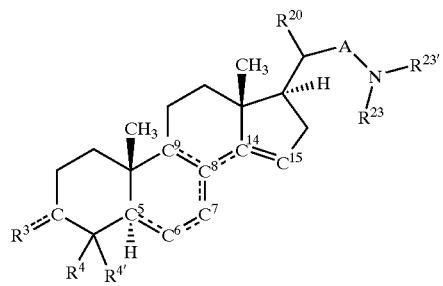

Especially the $\Delta^5$-pregnene derivatives, the $\Delta^{8,14}$-pregnadien derivatives, the $\Delta^8$-pregnene derivatives and the $\Delta^{5,7}$-pregnadiene derivatives are useful as pharmaceutically active steroid compounds for regulating reproduction, e.g. meiosis, i.e. compounds having the following general formulae:

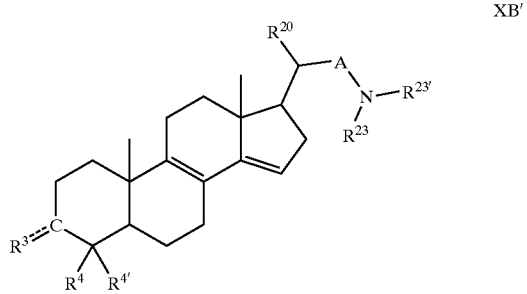

XB'

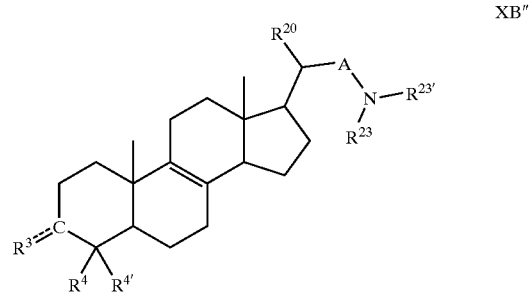

XB''

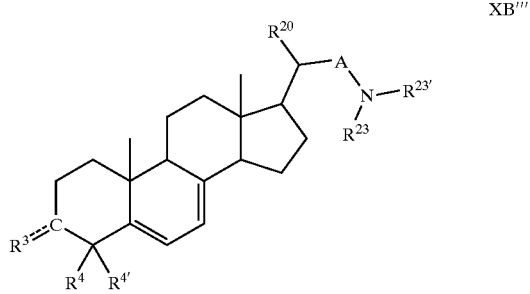

XB'''

-continued

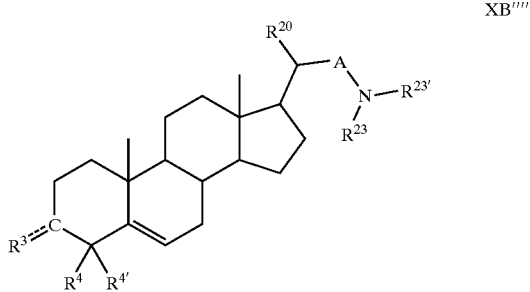

XB''''

It has surprisingly been found that the compounds according to the present invention have a strong meiosis stimulating effect in oocytes, especially in CEO, though these compounds are structurally highly different to sterol FF-MAS. In this respect the compounds of this invention are superior to this formerly described meiosis-regulating substance [e.g.: A. G. Byskov et al., *Nature*, 374, 559–562 (1995)]. Preferred compounds of general formula X are those, which induce the germinal vesicle breakdown by at least 40%, preferably at least 60% and especially at least 80% when tested in an oocyte test as described in example 23.

The compounds according to the present invention are superior to the formerly described compounds in a second aspect: Whereas FF-MAS is not able to induce maturation in a follicle culture system, the compounds of the present invention are able to activate meiosis in this situation.

For this reason the novel steroid compounds can e.g. be employed for in-vivo use as well as for non-in-vivo use, which especially comprises in-vitro use. The steroid compounds are especially suitable for in-vitro and for in-vivo fertilization of mammals, especially of humans.

The outstanding properties of the novel compounds may be attributed to the amino group in the side chain linked to the $C^{17}$ carbon atom in the steroid skeleton via a $C_2$–$C_3$ alkylen spacer (including the $C^{20}$—$R^{20}$ group).

Especially preferred are compounds, wherein the moiety $C^3R^3$ is CH—OH, in particular a 3β-hydroxy radical bonded to the $C^3$ atom of the steroid skeleton. The moiety may also be CH—O—C(O)—$R^{3''}$ (=CH—O—$R^{3'}$, wherein $R^{3'}$ is C(O)—$R^{3''}$), wherein $R^{3''}$ is defined as before. In particular $R^3$ may be an ester radical of a monocarboxylic acid, of a dicarboxylic acid, of an inorganic acid or of any other acid, bonded to the $C^3$ atom of the steroid skeleton. Especially for $R^3$ being an ester radical of a dicarboxylic acid $R^{3''}$ may be $(CH_2)_n$—COOH, wherein n=1, 2, 3, 4, 5 or 6. The ester radical may also be formed from an inorganic acid such as phosphoric acid, sulfuric acid and sulphamic acid, further from a monocarboxylic acid such as acetic acid, propionic acid, n-butanoic acid, pivalic acid, benzoic acid, nicotinic acid and isonicotinic acid. In particular the ester radical may be formed from a dicarboxylic acid, such as from succinic acid and glutaric acid.

Further steroid compounds according to the present invention may also include derivatives, in which C—O—$R^3$ represents a cyclic ether including the $C^3$ atom of the steroid skeleton.

$R^3$ may also form a cyclic ring structure together with the $C^3$ atom, $R^3$ being unsubstituted or substituted, linear or branched $C_2$–$C_{10}$ alkylen. E.g. $C^3R^3$ may be a cyclopropylen, cyclobutylen, cyclopentylen or cyclohexylen radical. It may also represent an unsaturated cyclic ring structure such as cyclopropenylen, cyclobutenylen, cyclopentenylen and cyclohexenylen. The ring structure may also be substituted by any of halogen, hydroxy, alkoxy, aryloxy and the like.

Substances according to the present invention may advantageously also be compounds, in which $R^{3''}$ is selected from the group comprising fluoromethyl, aryl, heteroaryl and $(CH_2)_n$—COOH, wherein n=1, 2, 3, 4, 5 or 6, especially compounds, in which $R^{3''}$ (=C(O)—$R^{3''}$) is acetyl, propionyl, pivaloyl, butanoyl, benzoyl, nicotinyl, isonicotinyl, hemi glutaroyl, butylcarbamoyl, phenylcarbamoyl, ethoxycarbonyl and tert-butoxycarbonyl. In a particularly preferred steroid compound $R^{3'}$ may be hemi succinoyl.

Further in the novel steroid compounds $R^4$ and $R^{4'}$, independently, are preferably hydrogen or a linear or branched $C_1$–$C_4$ alkyl group, i.e. methyl, ethyl, propyl and butyl, and especially methyl.

Further $R^4$ and $R^{4'}$, independently, may also be $C_1$–$C_4$ alkyl, substituted by halogen, hydroxy, alkoxy or aryloxy.

$R^{20}$ is preferably hydrogen or linear or branched $C_1$–$C_4$ alkyl, i.e. methyl, ethyl, propyl and butyl. $R^{20}$ is especially methyl.

$R^{23}$ and $R^{23'}$, independently, may specifically be hydrogen or a $C_1$–$C_8$ alkyl group, such as methyl, ethyl, n-propyl, iso-propyl, n-butyl, iso-butyl, tert-butyl, n-pentyl, iso-pentyl, tert-pentyl, neo-pentyl, further hexyl and cyclohexyl and the like. Further $R^{23}$ and $R^{23'}$, independently, may also be a $C_2$–$C_8$ alkenyl group, i.e. an unsaturated alkyl group, e.g. vinyl, allyl, iso-propenyl and prenyl, further $C_6$–$C_{10}$ aryl, such as phenyl and 1-naphthyl, this group also comprising alkylaryl, being bonded via the aryl moiety or via the alkyl moiety to the nitrogen atom, e.g. benzyl and tolyl. $R^{23}$ and $R^{23'}$ may preferably be alkyl and alkenyl, being substituted by at least one radical, selected from the group, comprising linear or branched $C_1$–$C_4$ alkyl and $C_1$–$C_4$ alkoxy. The phenyl and 1-naphthyl radical may also be substituted by halogen, $C_1$–$C_4$ alkoxy, hydroxy or $C_1$–$C_4$ alkyl, including the fluoroalkoxy and fluoroalkyl derivatives. Further $R^{23}$ and $R^{23'}$, independently, may further be e.g. 4-hydroxyphenyl, 4-methoxyphenyl, 2,4,6-trimethylphenyl, 2,4-dichlorophenyl, 4-fluorophenyl, 4-trifluoromethylphenyl and 2-pentafluoroethylphenyl.

Further $R^{23}$ and $R^{23'}$, independently, may also represent alkyl and alkenyl, at least one of the alkyl and alkenyl carbon atoms, respectively, being replaced by any of O, N and S, e.g. methoxymethylen, methoxyethylen, methoxypropylen, ethoxypropylen and the like.

$R^{23}$ and $R^{23'}$ together may also form a heterocyclic ring structure bonded to the side chain via the nitrogen atom in the side chain, the nitrogen atom being linked to the $C^{20}$ carbon atom of the steroid skeleton via the spacer group A. This heterocyclic ring structure, formed by $N(R^{23})(R^{23'})$, may especially be a moiety being selected from the group, comprising piperidin-1-yl, morpholin-4-yl, piperazin-1-yl, pyrrolidin-1-yl, pyrrol-1-yl, indol-1-yl, pyrazol-1-yl, imidazol-1-yl, thiazolidin-1-yl and oxazolidin-3-yl ring structures and substituted derivatives thereof. Especially preferred heterocyclic ring structures are the saturated radicals, namely piperidin-1-yl, morpholin-4-yl, piperazin-1-yl and pyrrolidin-1-yl. The heterocyclic ring structures may be substituted with hydroxy, carboxy, amino, alkylamino, dialkylamino, alkyl, alkenyl, alkynyl, cycloalkyl, cycloalkenyl, alkylcycloalkyl, aryl, alkylaryl, hydroxy, alkoxy, alkylcycloalkyloxy, alkyloxycycloalkyl, alkylaryloxy, alkyloxyaryl, halogen and acyl, wherein alkyl, alkenyl, alkynyl, cycloalkyl, aryl, alkoxy and acyl have a number of carbon atoms as indicated above. The heterocyclic ring structure may also be substituted with heterocyclic radicals, such as the heterocyclic ring structures to which they may be bonded and in addition to these as the further radicals, e.g. pyridinyl, chinolinyl, isochinolinyl, pyridazinyl, pyrimidinyl, pyrazinyl, chinoxalinyl, thiazolyl and oxazolyl, further including all other isomers of these radicals, e.g. pyridin-2-yl, pyridin-3-yl and pyridin-4-yl. Further if $N(R^{23})(R^{23'})$ is a heterocyclic ring structure this ring structure may also include an oxo group in the ring.

If $N(R^{23})(R^{23'})$ is piperazin-1-yl this moiety may be especially substituted by pyridin-2-yl, pyridin-3-yl and pyridin-4-yl, to preferably give the respective $N(R^{23})(R^{23'})$ groups in which the piperazin-1-yl group is substituted in para-position, e.g. 4-(pyridin-3-yl)piperazin-1-yl.

$N(R^{23})(R^{23'})$ may also be any of the moiety

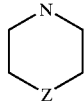

bonded to $C^{20}$ in the side chain of the steroid skeleton via the nitrogen atom of this moiety, wherein Z=O, S, N—$R^{24}$, N—C(O)—$R^{24}$, wherein $R^{24}$ is alkyl, alkenyl, alkynyl, aryl, the number of carbon atoms of which is defined as above. Further $R^{24}$ may be a heterocyclic ring structure, wherein the number of ring atoms is as defined above.

The nitrogen atom of $N(R^{23})(R^{23'})$ is not bonded directly but via A to the $C^{20}$ atom, wherein A is an unsubstituted or substituted methylen or ethylen spacer group, such as e.g. (unsubstituted) methylen and (unsubstituted) ethylen and further iso-propylen, tert-butylen and the like. Preferably A is methylen and ethylen.

Especially preferable are compounds, in which $R^3$ is hydroxy or hemi succinate ester, in which $R^4$, $R^{4'}$ and $R^{20}$ are each methyl and in which the heterocyclic ring structure $N(R^{23})R^{23'})$ including the amino nitrogen atom is an unsubstituted or substituted morpholin-4-yl, piperidin-1-yl, piperazin-1- or pyrrolidin-1-yl. $N(R^{23})(R^{23'})$ is in particular 3-hydroxypiperidin-1-yl, 4-hydroxy-piperidin-1-yl, 3-ketopiperidin-1-yl, 4-ketopiperidin-1-yl, 4-dimethylminopiperidin-1-yl, 3,3-dimethylpiperidin-1-yl, 4,4-dimethylpiperidin-1-yl, 3-carboxypiperidin-1-yl, 4-carboxy-piperidin, 4-phenylpiperidin-1-yl, 4-benzoylpiperidin-1-yl, 4-(piperidin-1-yl)piperidin-1-yl, 4-methylpiperazin-1-yl, 4-acetylpiperazin-1-yl, 4-phenylpiperazin-1-yl, 4-benzylpiperazin-1-yl, 4-benzoylpiperazin-1-yl, 4-(pyridin-2-yl)piperazin-1-yl, 4-(pyridin-4-yl)piperazin-1-yl, 4-(pyrimidin-2-yl)piperazin-1-yl.

Hydrogen atoms may be bonded to all other skeleton C atoms of the steroid compounds, i.e. to $C^1$, $C^2$, $C^6$, $C^7$, $C^8$, $C^9$, $C^{11}$, $C^{12}$, $C^{14}$, $C^{15}$ and $C^{16}$.

Preferably pharmaceutically acceptable compounds of the present invention are salts of steroid compounds of general formula X. Examples of these salts are listed in *Journal of Pharmaceutical Science*, 66, 2 et seq. (1977), which are hereby incorporated by reference. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid, methane sulphonic acid and the like. Suitable inorganic acids to form pharmaceutically acceptable salts include hydrochloric acid, hydrobromic acid, sulfuric acid, phosphoric acid and the like.

Figure 1C:
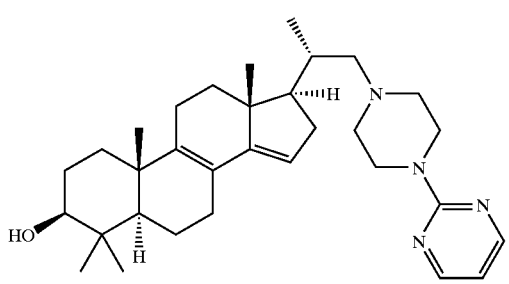
Figure 1C:
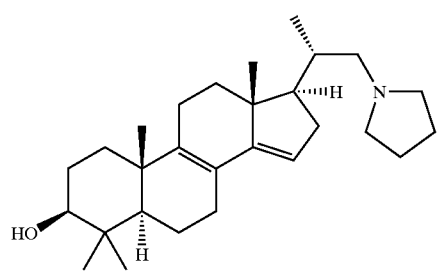
Figure 1C:
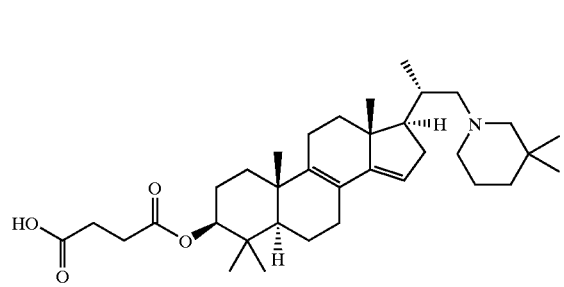
Figure 1C:
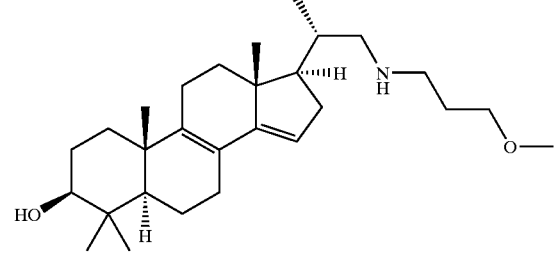
Figure 1C:
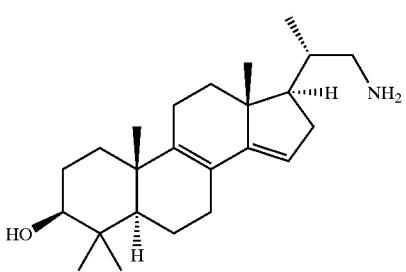
Figure 1E:
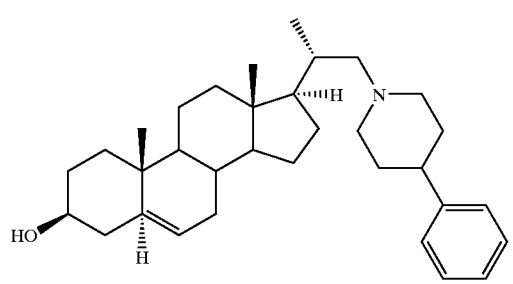
Figure 1E:
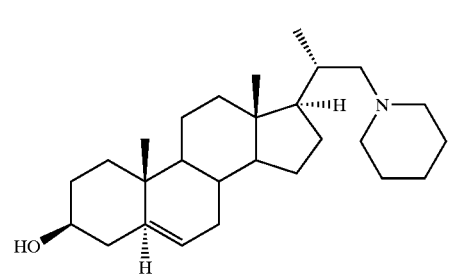
Figure 1E:
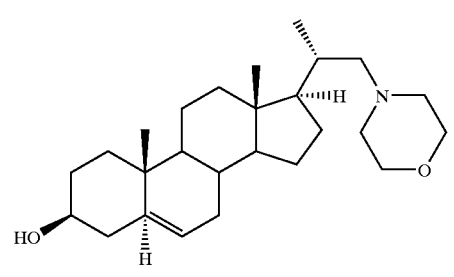
Figure 1E:
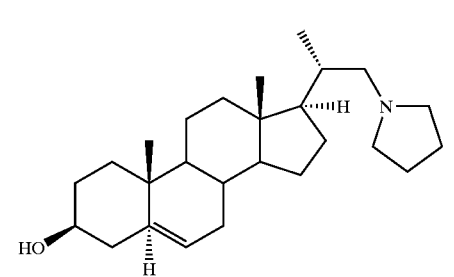
Figure 1E:
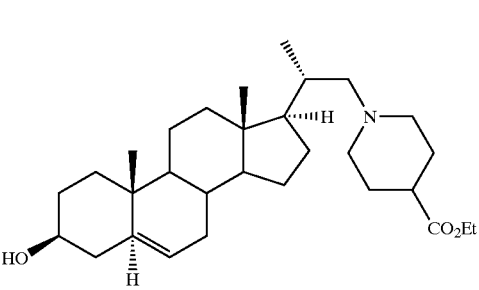
Figure 1F:
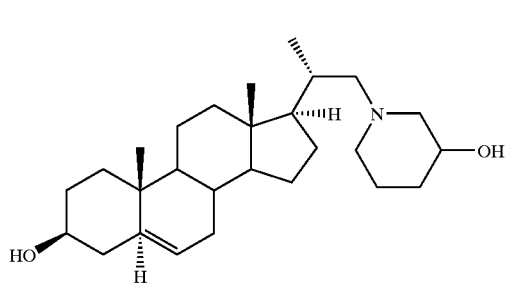
Figure 1F:
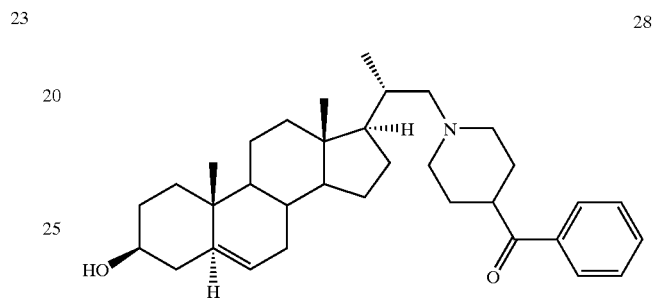
Figure 1F:
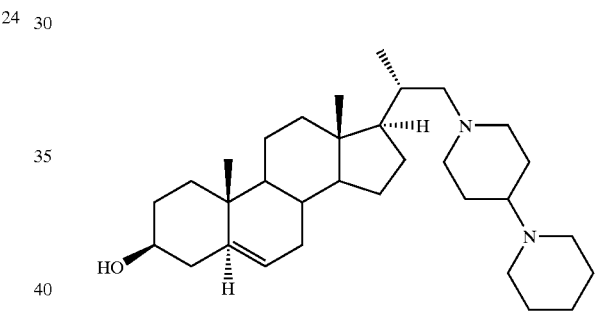
Figure 1F:
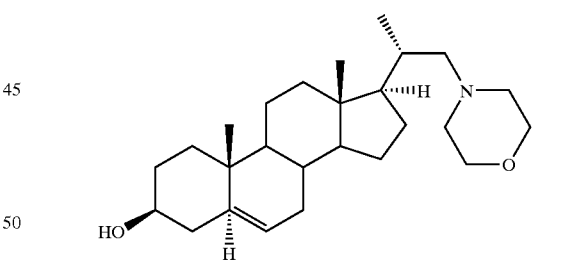
Figure 1F:
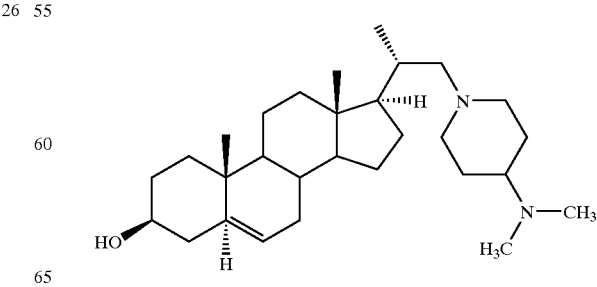
Figure 1G:
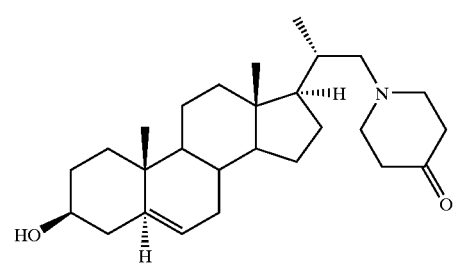
Figure 1G:
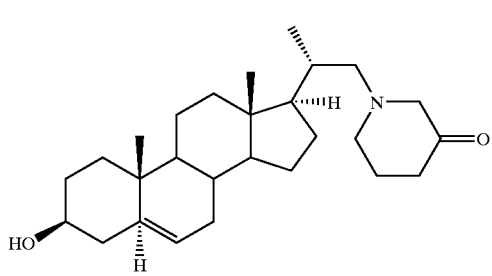
Figure 1G:
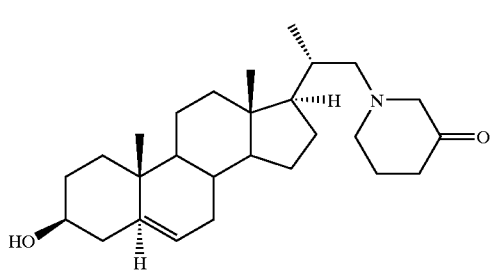
Figure 1G:
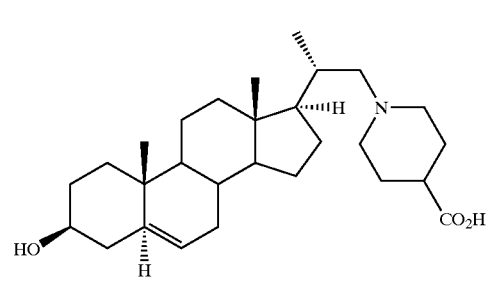
Figure 1G:
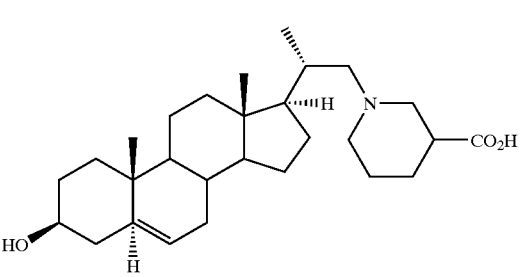
Figure 1H:
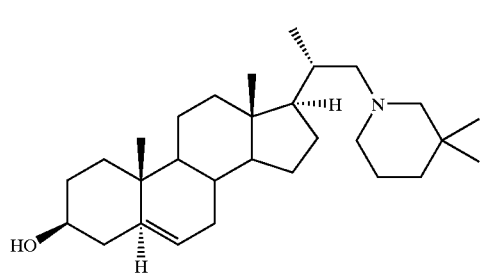
Figure 1H:
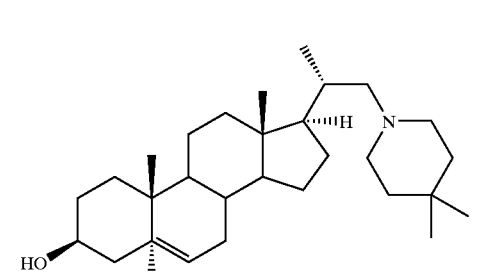
Figure 1H:
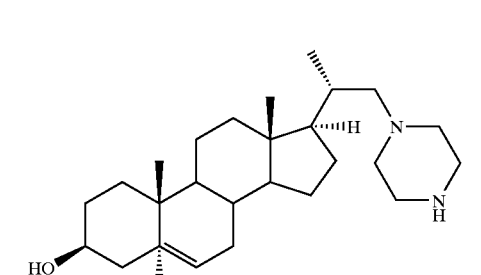
Figure 1H:
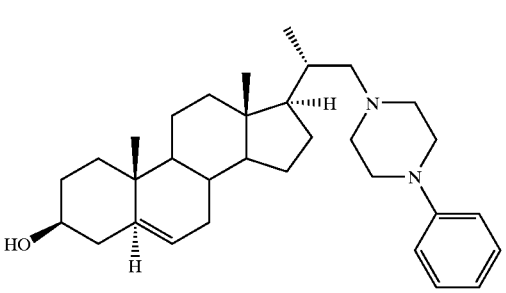
Figure 1H:
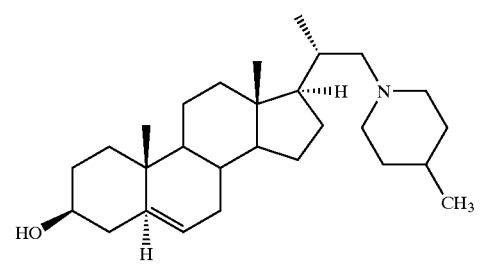

The following compounds according to the present invention are especially preferred:
1) (20S)-20-[(3,3-dimethylpiperidin-1-yl)methyl]-4,4-dimethyl-5α-pregna-8,14-dien-3β-ol
2) (20S)-20-[(piperidin-1-yl)methyl]-4,4-dimethyl-5α-pregna-8,14-dien-3β-ol
3) (20S)-20-[(4,4-dimethylpiperidin-1-yl)methyl]-4,4-dimethyl-5α-pregna-8,14-dien-3β-ol
4) (20S)-20-[(4-methylpiperazin-1-yl)methyl]-4,4-dimethyl-5α-pregna-8,14-dien-3β-ol
5) (20S)-20-[(4-phenylpiperazin-1-yl)methyl]-4,4-dimethyl-5α-pregna-8,14-dien-3β-ol
6) (20S)-20-[(morpholin-4-yl)methyl]-4,4-dimethyl-5α-pregna-8,14-dien-3,6-ol
7) (20S)-20-[(4-(pyrimidin-2-yl)piperazin-1-yl)methyl]-4,4-dimethyl-5α-pregna-8,14-dien-3β-ol
8) (20S)-20-[(pyrrolidin-1-yl)methyl]-4,4-dimethyl-5α-pregna-8,14-dien-3β-ol
9) (20S)-20-[(3,3-dimethylpiperidin-1-yl)methyl]-4,4-dimethyl-5α-pregna-8,14-dien-3β-ol hemisuccinate
10) (20S)-20-[N-(3-methoxypropyl)aminomethyl]-4,4-dimethyl-5α-pregna-8,14-dien-3β-ol
11) (20S)-20-aminomethyl-4,4-dimethyl-5α-pregna-8,14-dien-3β-ol
12) (20S)-20-[N,N-di-(2-methoxyethyl)aminomethyl]-4,4-dimethyl-5α-pregna-8,14-dien-3β-ol
13) (20S)-20-[N-(2,2-dimethylethylen)aminomethyl]-4,4-dimethyl-5α-pregna-8,14-dien-3β-ol
14) (20S)-20-[(piperidin-1-yl)methyl]-4,4-dimethyl-5α-pregna-5,7-dien-3β-ol
15) (20S)-20-[(4-(pyridin-2-yl)piperazin-1-yl)ethyl]-4,4-dimethyl-5α-pregna-8,14-dien-3β-ol
16) (20S)-20-[(4-phenylpiperazin-1-yl)ethyl]-4,4-dimethyl-5α-pregna-8,14-dien-3β-ol
17) (20S)-20-[(4-methylpiperazin-1-yl)ethyl]-4,4-dimethyl-5α-pregna-8,14-dien-3β-ol
18) (20S)-20-[(N,N-dimethylamino)ethyl]-4,4-dimethyl-5α-pregna-8,14-dien-3β-ol
19) (20S)-20-[(morpholin-4-yl)ethyl]-4,4-dimethyl-5α-pregna-8,14-dien-3β-ol
20) (20S)-20-[(pyrrolidin-1-yl)ethyl]-4,4-dimethyl-5α-pregna-8,14-dien-3β-ol
21) (20S)-20-[(piperidin-1-yl)ethyl]-4,4-dimethyl-5α-pregna-8,14-dien-3β-ol
22) (20S)-20-[(4-phenylpiperidin-1-yl)methyl]-5α-pregna-5-en-3β-ol
23) (20S)-20-[(piperidin-1-yl)methyl]-5α-pregna-5-en-3β-ol
24) (20S)-20-[(morpholin-4-yl)methyl]-5α-pregna-5-en-3β-ol
25) (20S)-20-[(pyrrolidin-1-yl)methyl]-5α-pregna-5-en-3β-ol
26) (20S)-20-[(4-carboxyethylpiperidin-1-yl)methyl]-5α-pregna-5-en-3β-ol
27) (20S)-20-[(3-hydroxypiperidin-1-yl)methyl]-5α-pregna-5-en-3β-ol
28) (20S)-20-[(4-benzoylpiperidin-1-yl)methyl]-5α-pregna-5-en-3β-ol
29) (20S)-20-[(4-(piperidin-1-yl)piperidin-1-yl)methyl]-5α-pregna-5-en-3β-ol
30) (20S)-20-[(4-thiomorpholinyl)methyl]-5α-pregna-5-en-3β-ol
31) (20S)-20-[(4-dimethylaminopiperidin-1-yl)methyl]-5α-pregna-5-en-3β-ol
32) (20S)-20-[(4-ketopiperidin-1-yl)methyl]-5α-pregna-5-en-3β-ol
33) (20S)-20-[(3-ketopiperidin-1-yl)methyl]-5α-pregna-5-en-3β-ol
34) (20S)-20-[(4-carboxylpiperidin-1-yl)methyl]-5α-pregna-5-en-3β-ol
35) (20S)-20-[(3-carboxylpiperidin-1-yl)methyl]-5α-pregna-5-en-3β-ol 36) (20S)-20-[(4-hydroxypiperidin-1-yl)methyl]-5α-pregna-5-en-3β-ol
37) (20S)-20-[(3,3-dimethylpiperidin-1-yl)methyl]-5α-pregna-5-en-3β-ol.
38) (20S)-20-[(4,4-dimethypiperidin-1-yl)methyl]-5α-pregna-5α-en-3β-ol
39) (20S)-20-[(4-piperazin-1-yl)methyl]-5α-pregna-5-en-3β-ol
40) (20S)-20-[(4-phenylpiperazin-1-yl)methyl]-5α-pregna-5-en-3β-ol
41) (20S)-20-[(4-methylpiperazin-1-yl)methyl]-5α-pregna-5-en-3β-ol
42) (20S)-20-[(4-benzylpiperazin-1-yl)methyl]-5α-pregna-5-en-3β-ol
43) (20S)-20-[(4-acetylpiperazin-1-yl)methyl]-5α-pregna-5-en-3β-ol
44) (20S)-20-[(4-benzoylpiperazin-1-yl)methyl]-5α-pregna-5-en-3β-ol
45) (20S)-20-[{4-(2-pyridyl)piperazin-1-yl}methyl]-5α-pregna-5-en-3β-ol
46) (20S)-20-[{4-(3-pyridyl)piperazin-1-yl}methyl]-5α-pregna-5-en-3β-ol
47) (20S)-20-[{4-(4-pyridyl )piperazin-1-yl}methyl]-5α-pregna-5-en-3β-ol
48) (20S)-20-[{4-(2-pyrimidyl)piperazin-1-yl}methyl]-5α-pregna-5-en-3β-ol
49) (20S)-20-[(piperidin-1-yl)methyl]-4,4-dimethyl-5α-pregna-$\Delta^{8(14)}$-en-3β-ol The structural formulae of these steroid compounds are shown in FIG. 1A–FIG. 1K.

A further object of the present invention are pharmaceutical compositions comprising at least one steroid compound of general formula X and at least one pharmaceutically acceptable excipient well known in the art, e.g. at least one carrier, diluent, absorption enhancer, preservative, buffer, agent for adjusting the osmotic pressure and rheology of the medicament if it will be liquid, surfactant, solvent, tablet disintegrating agent, micro capsules, filler, slip additive, colorant, flavour and other ingredient. These substances are conventionally used in the art. The steroid compounds according to the present invention are preferably comprised in the pharmaceutical compositions in an effective amount.

Examples for solid carriers are magnesium carbonate, magnesium stearate, dextrin, lactose, sugar, talkum, gelatin, pectin, starch, silica gel, tragacanth, methylcellulose, sodium carboxymethyl cellulose, low melting waxes and cacao butter.

Liquid compositions include sterile solutions, suspensions and emulsions, which may be administered e.g. orally by nasal administration or as an ointment. Such liquid compositions may also be suitable for injection or for use in connection with ex vivo or in vivo application. For oral administration the liquid may contain a pharmaceutically acceptable oil and/or lipophilic, surfactant and/or solvent which is miscible with water. In this connection reference is made to WO 97/21440 A1, which is hereby incorporated by reference.

Liquid compositions may also contain other ingredients, which are conventionally used in the art, some of which are mentioned in the list above. Further a composition for transdermal administration of a compound of the present invention may be provided in the form of a patch. A composition for nasal administration may be provided in the form of a nasal spray in liquid or in powder form.

In order to enhance bioavailability of the steroid compound these compounds may also be formulated as cyclodextrin chlatrates. For this purpose the compounds are compounded with α-, β- or γ-cyclodextrin or derivatives thereof.

Salves, ointments, lotions and other liquids to be administered externally must be in a condition such that the steroid compounds of the present invention may be delivered to the subject in need of regulation of meiosis in sufficient quantity. For this purpose the medicament contains excipients for regulating the rheology of the medicament, surfactants, preservatives, solvents, diluents, substances for enhancing skin permeation ability, further flavours and protective skin substances such as conditioners and moisture regulators.

The medicament may also contain further active agents to enhance or regulate the effectiveness of the steroid compounds or to produce other desired effects of the medicament.

For parenteral administration the steroid compounds may be dissolved or suspended in a pharmaceutically acceptable diluent. Oils are very often used in combination with solvents, surfactants, suspension or emulsion agents, e.g. olive oil, peanut oil, soybean oil, caster oil and the like. For the preparation of an injectable medicament any liquid carrier may be employed. These liquids often also contain agents for the regulation of the viscosity thereof as well as agents for regulating isotonicity of the liquid.

The steroid compound according to the present invention may further be administered as an injectable depot or as an implantate, which may e.g. be administered subcutanely, such that delayed release of the steroid compounds is made possible. For this purpose various techniques may be employed, e.g. administration of depots, which include a membrane containing the active compound, or of slowly dissolving depots. Implantates may e.g. contain biologically degradable polymers or synthetic silicones as inert material.

The dose of a steroid compound to be used will be determined by a physician and will depend inter alia on the particular steroid compound employed, on the route of administration and on the purpose of the use. In general, the compositions of the present invention are prepared by intimately bringing into association the active compound with the liquid or solid auxiliary ingredients and then, if necessary, shaping the product into the desired formulation.

Usually not more than 3000 mg, preferably not more than 350 mg, and in some preferred instances not more than 30 mg of the steroid compounds are to be administered to mammals, e.g. to humans, per day.

The present invention also relates to the use of the steroid compounds of general formula X for the preparation of a composition useful to regulate reproduction, e.g. meiosis. Preferably this composition is applicable as a medicament.

The present invention further relates to a use of the novel steroid compounds of general formula X to the preparation of a contraceptive or of a profertility drug.

The present invention further relates to the use of the steroid compound of general formula X for non-in-vivo use.

The present invention also relates to a method of regulating reproduction, e.g. meiosis, comprising administering to a subject in need of such a regulation an effective amount of at least one steroid compound of general formula X.

Further the present invention relates to a method for improving the possibility of an oocyte's ability to develop into a mammal, comprising contacting an oocyte removed from the mammal with the steroid compound of general formula X.

Regulation of reproduction, e.g. of meiosis, is used herein to indicate that the compounds according to the present invention are especially suitable to stimulate reproduction, e.g. meiosis, in mammal, especially human, oocytes such that these compounds which are agonistic analogues of a naturally occurring meiosis activating substance, can be used in the treatment of infertility which is due to insufficient stimulation of meiosis in females and males.

The route of administration of compositions containing a compound of the present invention may be any route, which effectively transports the active steroid compound to its site of action.

Thus, when the steroid compounds are to be administered to a mammal, they are conveniently provided in the form of a pharmaceutical composition, which comprises at least one steroid compound according to the present invention in connection with a pharmaceutically acceptable carrier. For oral use, such compositions are preferably in the form of tablets or capsules.

The present invention also relates to a method for the preparation of steroid compounds of general formula X, wherein $R^4$ and $R^{4'}$ are unsubstituted or substituted, linear or branched $C_1$–$C_4$ alkyl and not hydrogen:

The aforementioned steroid compounds may be synthesized analogously with the preparation of known compounds. Hence, synthesis of the steroid compounds of formula X may follow the well established synthetic pathways described in the comprehensive sterol and steroid literature. The following literature may be used as the key source for synthesis: L. F. Fieser & M. Fieser: *Steroids*, Reinhold Publishing Corporation, N.Y., 1959; *Rood's Chemistry of Carbon Compounds* (ed. S. Coffrey): Elsevier Publishing Company, 1971; and especially *Dictionary of Steroids* (eds. R. A. Hill, D. N. Kirk, H. L. J. Makin and G. M. Murphy), Chapman & Hall, this literature hereby incorporated by reference. The last one contains an extensive list of citations to the original papers covering the period up to 1990.

Particularly, the steroid compounds may be synthesized e.g. according to the general procedure, comprising
a. starting from (20S)-20-hydroxymethyl-pregna-4-en-3-one,
b. introducing two alkyl groups in position 4 by alkylation,
c. reducing the keto group to a hydroxy group,
d. introducing a $\Delta^7$ double bond by bromination/dehydrobromination,
e. isomerizing the dien $\Delta^{5,7}$ to the dien $\Delta^{8,14}$ by heating in the presence of acid,
f. oxidizing the 17-hydroxy group to an aldehyde group and
g. reductively aminizing the aldehyde group.

Figures 1I, 1K, 2:
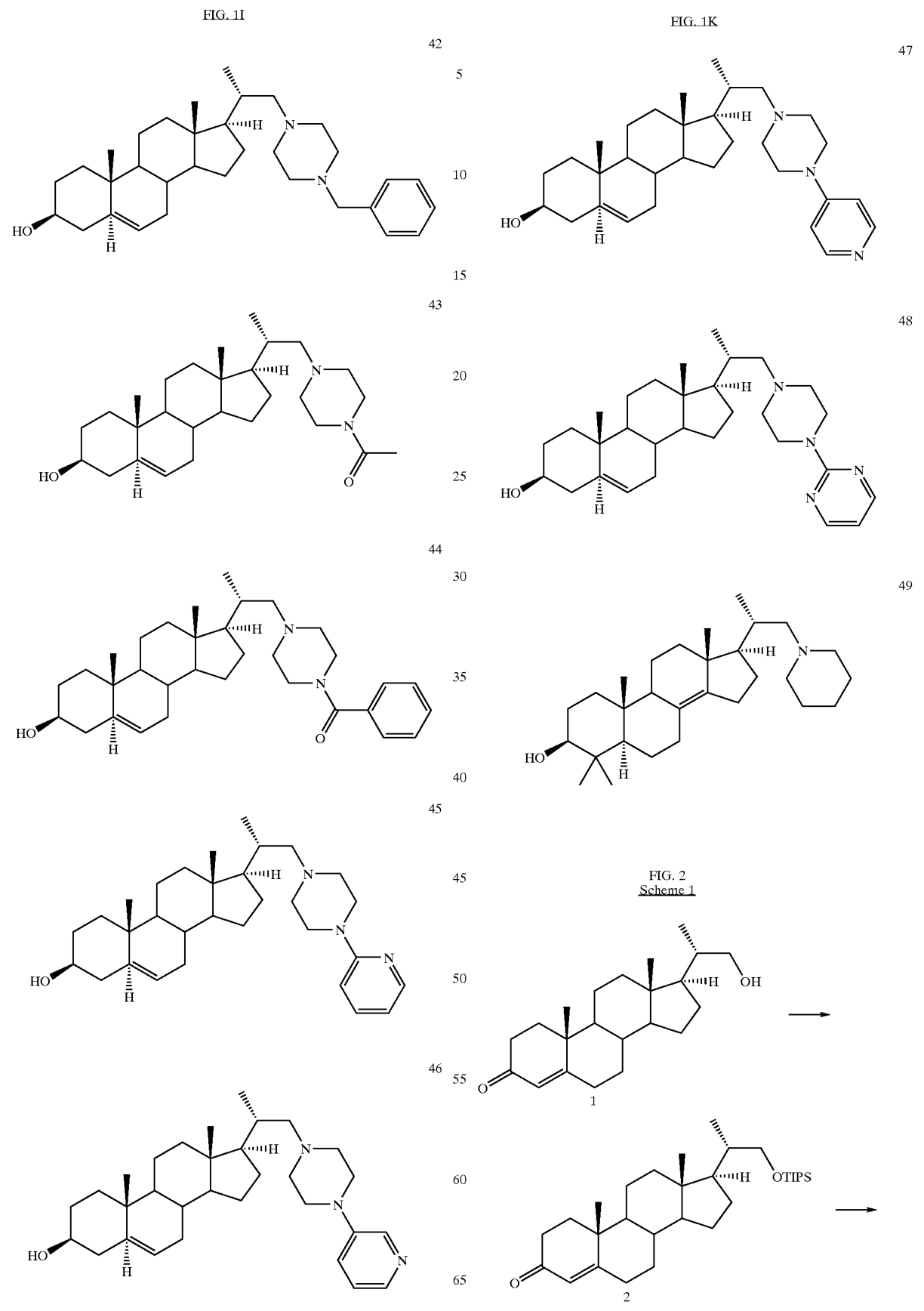

The corresponding synthesis scheme of this first synthesis method is shown in FIG. 2. According to this, first the hydroxy group in the side chain of (20S)-20-hydroxymethyl-pregna-4-en-3-one 1 is protected as a silylether, e.g. as a triisopropylsilyl (TIPS) ether resulting in compound 2. In order to produce compound 3 two methyl groups are introduced via alkylation with methyl iodide in the presence of a base like potassium tert-butoxide in position 4 of the steroid skeleton. In the next step the 3-keto group is reduced with a common reducing agent such as lithium aluminiumhydride or sodium borohydride. The resulting alcohol 4 is then protected e.g. as an acetate (compound 5). A second double bond is afterwards introduced via a bromination-dehydrobromination sequence. The resulting $\Delta^{5,7}$-dien system in compound 6 is then isomerized to the $\Delta^{8,14}$-dien system via heating in the presence of hydrochloric acid to obtain compound 7. In this acid catalyzed step both hydroxyl groups are deprotected and diol 7 can be obtained. Moderately selective oxidation of the hydroxyl group in the side chain with Dess-Martin Periodinane results in aldehyde 8, which serves as a central intermediate to introduce different amines in the side chain via reductive amination. For this purpose different reducing agents like sodium borohydride or tris-(acetoxy) borohydride may be used. As a result the steroid compounds 9 according to the present invention are obtained.

In the method for the preparation of the steroid compounds according to the present invention novel compounds are produced, namely: (20S)-4,4-dimethyl-20-hydroxymethyl-5α-pregna-8,14-dien-3β-ol and (20S)-4,4-dimethyl-5α-pregna-8,14-dien-3β-ol-20-carbaldehyde. Therefore the present invention also relates to these intermediate compounds.

Alternatively the steroid compounds may also be synthesized by the following procedure:
a. starting from a (20S)-20-trimethyl-pregna-8,14-dien-3β,21-diol, especially from (20S)-4,4,20-trimethyl-pregna-8,14-dien-3β,21-diol,
b. nucleophilic substitution at $C^{21}$, preferentially with a toluenesulfonic acid, to give the respective tosylate,
c. substituting the nucleophilic group (tosylate) at $C^{21}$ with cyanide to form a new carbon-carbon bond at $C^{21}$,
d. reducing the nitrile formed to give an aldehyde,
e. reductively aminating the nitrile to form various amines.

The corresponding synthesis scheme of this second synthesis method is shown in FIG. 3. The (20S)-4,4,20-trimethyl-pregna-8,14-3β,21-diol 1 is tosylated with para-toluenesulfonic chloride at the side chain. The tosylate 2 is then substituted with cyanide as a C1-building block. The resulting nitrile 3 is reduced thereafter with diisobutylaluminium hydride to give the aldehyde 4. The aldehyde 4 is then reacted with an amine in a reductive amination reaction in the presence of sodium tris(acetoxy)borohydride. The resulting product 5 formed may be purified by standard column chromatography or by HPLC.

Examples are given to more detailedly describe the present invention.

EXAMPLE 1

(20S)-20-[(piperidin-1-yl)methyl]-4,4-dimethyl-5α-pregna-8,14-dien-3β-ol (Compound No. 2)

a) (20S)-20-[((triisopropylsilyl)oxy)methyl]-pregna-4-en-3-one

To a solution of 30 g of (20S)-20-[(hydroxymethyl)]-pregna-4-en-3-one and 13.5 g imidazole in 300 ml dichloromethane 26 ml of triisopropylsilylchloride were added dropwise at room temperature. The reaction mixture was stirred for 20 hours at the same temperature and then poured into water. The aqueous layer was extracted with ethyl acetate. The organic layers were combined, washed with brine, dried over sodium sulfate, filtered and concentrated under reduced pressure to give 45.4 g of crude (20S)-20-[((triisopropylsilyl)oxy)methyl]-pregna-4-en-3-one as a brown oil, which was used without further purification.

MS (Cl+): 487 (M+H).

b) (20S)-4,4-dimethyl-20-[((triisopropylsilyl)oxy)methyl]-pregna-5-en-3-one

A solution of 45.4 g of crude (20S)-20-[((triisopropylsilyl)oxy)methyl]-pregna-4-en-3-one in 320 ml tetrahydrofuran was added to a solution of 42.3 g potassium tert-butylate in 950 ml tert-butanol at a temperature of 50° C. The mixture was stirred for 10 minutes at the same temperature. Then 50 ml methyl iodide were added and stirring was continued for one hour. The reaction mixture was poured into water and extracted with ethyl acetate. The organic layers were combined, washed with brine, dried over sodium sulfate, filtered and concentrated under reduced pressure. The residue was purified by column chromatography to give 27.3 g (20S)-4,4-dimethyl-20-[((triisopropylsilyl)oxy)methyl]-pregna-5-en-3-one as a pale yellow solid MS (Cl+): 515 (M+H). .

c) (20S)-4,4-dimethyl-20-[((triisopropylsilyl)oxy)methyl]-pregna-5-en-3β-ol

To a solution of 27.3 g (20S)-4,4-dimethyl-20-[((triisopropylsilyl)oxy)methyl]-pregna-5-en-3-one in 500 ml tetrahydrofuran 1.24 g of lithiumaluminum hydride were added cautiously in small portions at room temperature. The reaction mixture was stirred for one hour and then cooled to 0°C. 2.5 ml water, 2.5 ml of a 1 N sodium hydroxide solution and 7.5 ml of water were added successively. The mixture was filtered over celite. The filtrate was concentrated under reduced pressure. The residue was purified by column chromatography to give 18.2 g (20S)-4,4-dimethyl-20-[((triisopropylsilyl)oxy)methyl]-pregna-5-en-3β-ol as a pale yellow solid.

MS (Cl+): 517 (M+H).

d) (20S)-4,4-dimethyl-20-[((triisopropylsilyl)oxy)methyl]-pregna-5-en-3β-ol acetate To a solution of 18.2 g (20S)-4,4-dimethyl-20-[((triisopropylsilyl)oxy)methyl]-pregna-5-en-3β-ol in 175 ml pyridine 6.24 ml of acetic anhydride were added at room temperature. The reaction mixture was stirred for 20 hours and then poured into an ice/hydrochloric acid mixture. This was extracted with ethyl acetate. The organic layers were combined, washed with brine, dried over sodium sulfate, filtered and concentrated under reduced pressure to give 16.2 g (20S)-4,4-dimethyl-20-[((triisopropylsilyl)oxy)methyl]-pregna-5-en-3-one acetate as a white solid, which was used without further purification.

MS (Cl+): 559 (M+H).

e) (20S)-4,4-dimethyl-20-[((triisopropylsilyl)oxy)methyl]-pregna-5,7-dien-3β-ol acetate To a solution of 16.2 g (20S)-4,4-dimethyl-20-[((triisopropylsilyl)oxy)methyl]-pregna-5-en-3β-ol acetate in a mixture of 100 ml benzene and 100 ml hexane 4.93 g 1,3-dibrom-5,5-dimethyl-hydantoin were added in portions at 70° C. After 30 minutes the mixture was cooled to 0°C. and filtered. The filtrate was evaporated in vacuo.

To the resulting residue 160 ml toluene and 7.8 ml 2,4,6-trimethylpridine were added. The mixture was refluxed for 2.5 hours. After cooling the reaction mixture was washed with 1 N hydrochloric acid, saturated sodium bicarbonate solution and brine. The organic layer was dried over sodium sulfate, filtered and evaporated in vacuo. The residue was purified by column chromatography to give 12.5 g (20S)-4,4-dimethyl-20-[((triisopropylsilyl)oxy)methyl]-pregna-5,7-dien-3β-ol acetate as a white solid.

MS (Cl+): 557 (M+H).

f) (20S)-4,4,20-trimethyl-pregna-8,14-dien-3β,21-diol

A mixture of 16.1 g (20S)-4,4-dimethyl-20-[((triisopropylsilyl)oxy)methyl]-pregna-5,7-dien-3β-ol acetate, 210 ml ethanol, 28 ml benzene and 28 ml concentrated hydrochloric acid was refluxed for 6 hours. After cooling the mixture was poured into saturated sodium bicarbonate solution, extracted with ethyl acetate and washed with brine. The organic layer was dried over sodium sulfate, filtered and concentrated under reduced pressure. The residue was recrystallized from dichloromethane and methanol to give 4.48 g (20S)-20-hydroxy-4,4,20-trimethyl-pregna-8,14-dien-3β-ol.

MS (El+): 358 (M).

g) (20S)-3β-hydroxy-4,4,20-trimethyl-pregna-8,14-dien-21-al

To a solution of 1 g (20S)-4,4,20-trimethyl-pregna-8,14-dien-3β,21-diol in 10 ml dichloromethane 5.4 ml of a 0.5 M Dess-Martin-Periodinane solution were added at room temperature. The mixture was stirred for one hour, poured into saturated sodium bicarbonate solution, extracted with ethyl acetate and washed with brine. The organic layer was dried over sodium sulfate, filtered and concentrated under reduced pressure. The residue was purified by column chromatography to give 230 mg (20S)-3β-hydroxy-4,4,20-trimethyl-pregna-8,14-dien-21-al as a white solid.

MS (El+): 356 (M).

h) (20S)-20-[(piperidin-1-yl)methyl]-4,4-dimethyl-5α-pregna-8,14-dien-3β-ol 38 mg sodium tris(acetoxy)borohydride were added to a solution of 42 mg (20S)-3β-hydroxy-4,4,20-trimethyl-pregna-8,14-dien-21-al and 10 μl piperidine in 3 ml tetrahydrofuran at room temperature. The mixture was stirred for two hours, poured into saturated sodium bicarbonate solution, extracted with ethyl acetate and washed with brine. The organic layer was dried over sodium sulfate, filtered and concentrated under reduced pressure. The residue was purified by column chromatography to give 15 mg (20S)-20-[(piperidin-1-yl)methyl]-4,4-dimethyl-5α-pregna-8,14-dien-3β-ol as a white solid.

MS (El+): 425 (M).

EXAMPLE 2

(20S)-20-[(3,3-dimethylpiperidin-1-yl)methyl]-4,4-dimethyl-5α-pregna-8,14-dien-3β-ol (20S)-3β-hydroxy-4,4,20-trimethyl-pregna-8,14-dien-21-al was treated with 3,3-dimethyl-piperidine and sodium tris(acetoxy)borohydride as described in Example 1h). (20S)-20-[(3,3-dimethylpiperidin-1-yl)methyl]-4,4-dimethyl-5α-pregna-8,14-dien-3β-ol was isolated as a white solid.

MS (El+): 453 (M).

EXAMPLE 3

(20S)-20-[(4-phenylpiperazin-1-yl)methyl]-4,4-dimethyl-5α-pregna-8,14-dien-3β-ol (Compound No. 5)

(20S)-3β-hydroxy-4,4,20-trimethyl-pregna-8,14-dien-21-al was treated with N-phenyl-piperazine and sodium tris (acetoxy)borohydride as described in Example 1h). (20S)-20-[(4-phenylpiperazin-1-yl)methyl]-4,4-dimethyl-5α-pregna-8,14-dien-3β-ol was isolated as a white solid.

MS (El+): 502 (M).

EXAMPLE 4

(20S)-20-[(morpholin-4-yl)methyl]-4,4-dimethyl-5α-pregna-8,14-dien-3β-ol (Compound No. 6)

(20S)-3β-hydroxy-4,4,20-trimethyl-pregna-8,14-dien-21-al was treated with morpholine and sodium tris(acetoxy)borohydride as described in Example 1h). (20S)-20-[(morpholin-4-yl)methyl]-4,4-dimethyl-5α-pregna-8,14-dien-3β-ol was isolated as a white solid.

MS (El+): 427 (M).

EXAMPLE 5

(20S)-20-[(4-(pyrimidin-2-yl)piperazin-1-yl)methyl]-4,4-dimethyl-5α-pregna-8,14-dien-3β-ol (Compound No. 7)

(20S)-3β-hydroxy-4,4,20-trimethyl-pregna-8,14-dien-21-al was treated with N-(pyrimidin-2-yl)piperazine and sodium tris(acetoxy)borohydride as described in Example 1h). (20S)-20-[(4-(pyrimidin-2-yl)piperazin-1-yl)methyl]-4,4-dimethyl-5α-pregna-8,14-dien-3β-ol was isolated as a white solid MS (El+): 504 (M). .

EXAMPLE 6

(20S)-20-[(pyrrolidin-1-yl)methyl]-4,4-dimethyl-5α-pregna-8,14-dien-3β-ol (Compound No. 8)

(20S)-3β-hydroxy-4,4,20-trimethyl-pregna-8,14-dien-21-al was treated with pyrrolidin and sodium tris(acetoxy)borohydride as described in Example 1h). (20S)-20-[(pyrrolidin-1-yl)methyl]-4,4-dimethyl-5α-pregna-8,14-dien-3β-ol was isolated as a white solid.

MS (El+): 411 (M).

EXAMPLE 7

(20S)-20-[N-(3-methoxypropyl)aminomethyl]-4,4-dimethyl-5α-pregna-8,14-dien-3β-ol (Compound No. 10)

(20S)-3β-hydroxy-4,4,20-trimethyl-pregna-8,14-dien-21-al was treated with 3-methoxypropylamine and sodium tris(acetoxy)borohydride as described in Example 1h). (20S)-20-[N-(3-methoxypropyl)aminomethyl]-4,4-dimethyl-5α-pregna-8,14-dien-3β-ol was isolated as a white solid.

MS (El+): 429 (M).

EXAMPLE 8

(20S)-20-[(piperidin-1-yl)methyl]-4,4-dimethyl-5α-pregna-5,7-dien-3β-ol (Compound No. 14)

a) (20S)-4,4 dimethyl-20-[((triisopropylsilyl)oxy)methyl]-pregna-5-en-3-ol benzoate 34.4 ml of benzoylchloride were added to a solution of 70 g crude (20S)-4,4-dimethyl-20-[((triisopropylsilyl)oxy)methyl]-pregna-5-en-3β-ol (Example 1c) (not purified by chromatography) in 670 mg pyridine at 0–3° C. The reaction mixture was stirred for 2 h at room temperature and poured into ice-water. The precipitate was filtered off, washed with water and recrystallized from acetone to give 42 g of (20S)-4,4-dimethyl-20-[((triisopropylsilyl)oxy)methyl]-pregna-5-en-3β-ol benzoate.

$^1$H-NMR (CDCl$_3$): δ=8.05 (2H, d); 7.56 (1H, t); 7.45 (2H, t); 5.60 (1H, t); 4.74 (1H, m); 3.68 (1H, dd); 3.36 (1H, m).

b) (20S)-4,4-dimethyl-20-[((triisopropylsilyl)oxy)methyl]-pregna-5,7-dien-3β-ol benzoate 42 g of (20S)-4,4-dimethyl-20-[((triisopropylsilyl)oxy)methyl]-pregna-5-en-3β-ol benzoate were treated with 13.7 g 1,3-dibrom-5,5-dimethyl-hydantoin and 18 ml 2,4,6-trimethylpyridine as described in Example 1e) to give (without purification by column chromatography) 41.9 g of (20S)-4,4-dimethyl-20-[((triisopropylsilyl)oxy)methyl]-pregna-5,7-dien-3β-ol benzoate.

$^1$H-NMR (CDCl$_3$): δ=8.05 (2H, d); 7.57 (1H, t); 7.45 (2H, t); 5.95 (1H, d); 5.56 (1H, m); 4.85 (1H, m); 3.7 (1H, dd); 3.39 (1H, m).

c) (20S)-4,4,20-trimethyl-pregna-5,7-dien-3β-1,21-diol 3-benzoate 2 g pulverized molecular sieve (4 Å) and 1.27 g tetrabutylammoniumfluoride hydrate were added to a solution of 2.0 g (20S)-4,4-dimethyl-20-[((triisopropylsilyl)oxy)methyl]-pregna-5,7-dien-3β-ol in 50 ml tetrahydrofuran were added. The mixture was stirred overnight at room temperature, concentrated under reduced pressure and purified by column chromatography to give 1.17 g of (20S)-4,4,20-trimethyl-pregna-5,7-dien-3β,21-diol benzoate.

$^1$H-NMR (CDCl$_3$): δ=8.06 (2H, d); 7.56 (1H, t); 7.45 (2H, t); 5.94 (1H, d); 5.56 (1H, m); 4.85 (1H, m); 3.66 (1H, m); 3.41 (1H, m).

d) (20S)-4,4-dimethyl-20-[((toluene-4-sulfonyl)oxy)methyl]-pregna-5,7-dien-3β-ol benzoate A solution of 0.573 g toluene-4-sulfonylchloride in 4 ml pyridine was added drop by drop to a solution of 0.926 g (20S)-4,4,20-trimethyl-pregna-5,7-dien-3β,21-diol 3-benzoate in 15 ml pyridine while cooling on an ice-bath. The reaction mixture was stirred for 1 h at 0–3□C. and overnight at room temperature. The reaction mixture was poured into ice-water and extracted with ethyl acetate. The organic layers were combined, washed with 1N hydrochloric acid, saturated sodium hydrogencarbonate solution and brine. The organic layer was dried over sodium sulfate, filtered and concentrated under reduced pressure to give 1.0 g of (20S)-4,4-dimethyl-20-[((toluene-4-sulfonyl)oxy)methyl]-pregna-5,7-dien-3β-ol benzoate which could be further purified by crystallization from methanol.

$^1$H-NMR (CDCl$_3$): δ=8.05 (2H, d); 7.8 (1H, d); 7.56 (1H, t); 7.45 (2H, t); 7.34 (2H, d); 5.94 (1H, d); 5.55 (1H, m); 4.85 (1H, m); 4.0 (1H, dd); 3.81 (1H, m); 2.45 (3H, s).

e) (20S)-20-[(piperidin-1-yl)methyl]-4,4-dimethyl-5α-pregna-5,7-dien-3β-ol benzoate 0.625 ml piperidine were added to a solution of 0.154 g (20S)-4,4-dimethyl-20-[((toluene-4-sulfonyl)oxy)methyl]-pregna-5,7-dien-3β-ol benzoate in 3 ml N,N-dimethylformamide. The reaction mixture was stirred for 48 h at room temperature and concentrated under reduced pressure. The residue was dissolved in dichloromethane and washed three times with water. The organic layer was dried over sodium sulfate, filtered and evaporated in vacuo.

The residue (125 mg) was crystallized from methanol to give 45 mg of (20S)-20-[(piperidin-1-yl)methyl]-4,4-dimethyl-5α-pregna-5,7-dien-3β-ol benzoate.

$^1$H-NMR (CDCl$_3$): δ=8.05 (2H, d); 7.57 (1H, t); 7.46 (2H, t); 5.94 (1H, d); 5.56 (1H, m); 4.88 (1H, t); 2.43 (2H, m).

f) (20S)-20-[(piperidine-1-yl)methyl]-4,4-dimethyl-5α-pregna-5,7-dien-3β-ol

A solution of 45 mg (20S)-20-[(piperidin-1-yl)methyl]-4,4-dimethyl-5α-pregna-5,7-dien-3β-ol benzoate in 2.5 ml tetrahydrofuran was added to a suspension of 45 mg lithium aluminium hydride in 2 ml tetrahydrofuran. After stirring for 2 h at room temperature, a 3 ml saturated sodium sulfate solution and 5 ml 1N sodium hydroxide were added. The mixture was extracted three times with 10 ml dichloromethane. The organic layers were combined, washed with 1N sodium hydroxide and water, dried over sodium sulfate, filtered and concentrated under reduced pressure. The residue (35 mg) was purified by column chromatography to give 22 mg (20S)-20-[(piperidin-1-yl)methyl]-4,4-dimethyl-5α-pregna-5,7-dien-3β-ol.

$^1$H-NMR (CDCl$_3$): δ=5.93 (1H, d); 5.53 (1H, m); 3.4 (1H, t); 2.42 (2H, m); 1.22 (3H, s); 1.13 (3H, s); 1.02 (3H, d); 0.98 (3H, s); 0.6 (3H, s).

EXAMPLE 9

(20S)-20-[(4-(pyridin-2-yl)piperazin-1-yl)ethyl]-4,4-dimethyl-5α-pregna-8,14-dien-3β-ol (Compound No. 15)

a) (20S)-4,4,20-trimethyl-21-tosyloxy-pregna-8,14-dien-3β-ol 4.7 g p-tosylchloride were added in small portions to a solution of 4.5 g (20S)-4,4,20-trimethyl-pregna-8,14-dien-3β,21-diol in 91 ml pyridine at room temperature. The mixture was stirred for 3 h at room temperature and then concentrated under reduced pressure. The residue was dissolved in ethyl acetate, washed with water and a solution of sodium chloride. The organic layer was dried over sodium sulfate, filtered and concentrated under reduced pressure.

The residue was purified by column chromatography to give 3.2 g (20S)-4,4,20-trimethyl-21-tosyloxy-pregna-8,14-dien-3β-ol as a white solid.

MS (El+): 512 (M).

b) (20S)-3β-hydroxy-4,4,20-trimethyl-pregna-8,14-dien-21-carbonitril 1.7 g potassium cyanide were added to a solution of 4.7 g (20S)-4,4,20-trimethyl-21-tosyloxy-pregna-8,14-dien-3β-ol in 90 ml DMSO at room temperature. The mixture was stirred for 2 h at 90° C., poured into water, extracted with ethyl acetate and washed with water. The organic layer was dried over sodium sulfate, filtered and concentrated under reduced pressure to give 2.8 g (20S)-3β-hydroxy-4,4,20-trimethyl-pregna-8,14-dien-21-carbonitril as a white solid which was used without further purification.

MS (El+): 367 (M).

c) (20S)-3β-hydroxy-4,4,20-trimethyl-pregna-8,14-dien-21-carbaldehyde 16 ml diisobutylaluminiumhydride (20% in toluene) were added dropwise to a solution of 920 mg (20S)-3β-hydroxy-4,4,20-trimethyl-pregna-8,14-dien-21-carbonitril in 60 ml toluene at a temperature of −72° C. The mixture was stirred for 2 h at the same temperature, poured into 2N sulfuric acid, extracted with ethyl acetate, washed with 2N sulfuric acid and then washed with a half saturated solution of sodium chloride. The organic layer was dried over sodium sulfate, filtered and concentrated under reduced pressure to give 750 mg (20S)-3β-hydroxy-4,4,20-trimethyl-pregna-8,14-dien-21-carbaldehyde as a white solid, which was used without further purification.

MS (El+): 370 (M).

d) (20S)-[(4-(pyridin-2-yl)piperazin-1-yl)ethyl]-4,4-dimethyl-5α-pregna-8,14-dien-3β-ol 107 mg sodium tris(acetoxy)borohydride were added to a solution of 125 mg (20S)-3β-4,4,20-trimethyl-pregna-8,14-dien-21-carbaldehyde and 82.6 mg N-(2-pyridyl)-piperazine in 2 ml tetrahydrofuran at room temperature. The mixture was stirred for 20 h, poured into water and concentrated under reduced pressure. The residue was purified by column chromatography to give 84 mg (20S)-20-[(piperidin-1-yl)methyl]-4,4-dimethyl-5α-pregna-8,14-dien-3β-ol as a white solid.

MS (El+): 517 (M).

EXAMPLE 10

(20S)-20-[(4-phenylpiperazin-1-yl)ethyl]-4,4-dimethyl-5α-pregna-8,14-dien-3β-ol (Compound No. 16)

(20S)-3β-hydroxy-4,4,20-trimethyl-pregna-8,14-dien-21-carbaldehyde was treated with N-phenylpiperazin and sodium tris(acetoxy)borohydride as described in Example 9d). (20S)-20-[(4-phenylpiperazin-1-yl)ethyl]-4,4-dimethyl-5α-pregna-8,14-dien-3β-ol was isolated as a white solid.

MS (El+): 516 (M).

EXAMPLE 11

(20S)-20-[(4-methylpiperazin-1-yl)ethyl]-4,4-dimethyl-5α-pregna-8,14-dien-3β-ol (Compound No. 17)

(20S)-3β-hydroxy-4,4,20-trimethyl-pregna-8,14-dien-21-carbaldehyde was treated with 1-methylpiperazin and sodium tris(acetoxy)borohydride as described in Example 9d). (20S)-20-[(4-methylpiperazin-1-yl)ethyl]-4,4-dimethyl-5α-pregna-8,14-dien-3β-ol was isolated as a white solid.

MS (El+): 454 (M).

EXAMPLE 12

(20S)-20-[(N,N-dimethylamino)ethyl]-4,4-dimethyl-5α-pregna-8,14-dien-3β-ol (Compound No. 18)

(20S)-3β-hydroxy-4,4,20-trimethyl-pregna-8,14-dien-21-carbaldehyde was treated with N,N-dimethylamin and sodium tris(acetoxy)borohydride as described in Example 9d). (20S)-20-[(N,N-dimethylamino)ethyl]-4,4-dimethyl-5α-pregna-8,14-dien-3β-ol was isolated as a white solid.

MS (El+): 399 (M).

EXAMPLE 13

(20S)-20-[(morpholin-4-yl)ethyl]-4,4dimethyl-5α-pregna-8,14-dien-3β-ol (Compound No. 19)

(20S)-3β-hydroxy-4,4,20-trimethyl-pregna-8,14-dien-21-carbaldehyde was treated with morpholine and sodium tris (acetoxy)borohydride as described in Example 9d). (20S)-20-[(morpholin-4-yl)ethyl]-4,4-dimethyl-5α-pregna-8,14-dien-3β-ol was isolated as a white solid.

MS (El+): 441 (M).

EXAMPLE 14

(20S)-20-[(pyrrolidin-1-yl)ethyl]-4,4-dimethyl-5α-pregna-8,14-dien-3β-ol (Compound No. 20)

(20S)-3β-hydroxy-4,4,20-trimethyl-pregna-8,14-dien-21-carbaldehyde was treated with pyrrolidine and sodium tris (acetoxy)borohydride as described in Example 9d). (20S)-20-[(pyrrolidin-1-yl)ethyl]-4,4-dimethyl-5α-pregna-8,14-dien-3β-ol was isolated as a white solid.

MS (El+): 425 (M).

EXAMPLE 15

(20S)-20-[(piperidin-1-yl)ethyl]-4,4-dimethyl-5α-pregna-8,14-dien-3β-ol (Compound No. 21)

(20S)-3β-hydroxy-4,4,20-trimethyl-pregna-8,14-dien-21-carbaldehyde was treated with piperidine and sodium tris (acetoxy)borohydride as described in Example 9d). (20S)-20-[(piperidin-1-yl-)ethyl]-4,4-dimethyl-5α-pregna-8,14-dien-3β-ol was isolated as a white solid.

MS (El+): 439 (M).

EXAMPLE 16

(20S)-20-[(4-phenylpiperidin-1-yl)methyl]-5α-pregna-5-en-3β-ol (Compound No. 22)

a) 3β-tert-butyldimethylsilyloxybisnorcholenic acid methyl ether

3β-hydroxybisnorcholenic acid (10 g), potassium bicarbonate (12 g), methyl iodide (10 ml) and dimethyl formamide were stirred for 3 days at room temperature and poured into water (1.5 ml). The white precipitate was filtered off. Diethylether was added to the white precipitate and unsoluble material was filtered off. Concentration of the ether phase in vacuo afforded the crude silyl ether which was dissolved in dimethyl formamide (400 ml). Tert-butyldimethylsilyl chloride (6 g) and imidazole (6 g) were added and the mixture was concentrated in vacuo and purified by flash chromatography to give 5.3 g of 3β-tert-butyldimethylsilyloxynorcholenic acid methyl ether.

b) 3β-tert-butyldimethylsilyloxy-(20S)-20-methyl-5α-pregna-5-en-21-ol 2.2 equivalents diisobutylaluminium hydride (2M) in toluene were added to 3β-tert-butyldimethylsilyloxybisnorcholenic acid methyl ether and the reaction mixture was stirred at room temperature. The reaction mixture was added to water, extracted using diethyl ether, concentrated in vacuo and purified by flash chromatography to give 3.3 g of 3β-tert-butyldimethylsilyloxy-(20S)-20-methyl-5α-pregna-5-en-21-ol.

c) 3β-tert-butyldimethylsilyloxy-(20S)-20-methyl-5α-pregna-5-en-21-al

Dess-Martin-Periodinane solution (1.9 g in 30 ml), dichloromethane were added to 1.6 g of 3β-tert-butyldimethylsilyloxy-(20S)-20-methyl-5α-pregna-5-en-21-ol in dichloromethane (30 ml) and the reaction mixture was stirred for 24 h, then poured into diethylether and extracted with 1N sodium hydroxide. The organic layer was dried over magnesium sulfate and concentrated in vacuo to give 1.6 g of 3β-tert-butyldimethylsilyloxy-(20S)-20-methyl-5α-pregna-5-en-21-al.

d) 3β-tert-butyldimethylsilyloxy-(20S)-20-[(4-phenylpiperidin-1-yl)methyl]-5α-pregna-5-ene 4-phenylpiperidine (0.16 g) was added to 0.26 g of 3β-tert-butyldimethylsilyloxy-(20S)-20-methyl-5α-pregna-5en-21-al in THF (20 ml), followed by sodium tris(acetoxy) borohydride (0.38 g). After 5 h the reaction mixture was poured into saturated sodium bicarbonate, extracted with ethyl acetate, dried and concentrated in vacuo. Flash chromatography gave 76 mg of 3β-tert-butyldimethylsilyloxy-(20S)-20-[(4-phenylpiperidin-1-yl)methyl]-5α-pregna-5-ene.

e) (20S)-20-[(4-phenylpiperidin-1-yl)methyl]-5α-pregna-5-en-3β-ol 6N hydrochloric acid (0.2 ml) was added to a mixture of 100 mg of 3β-tert-butyldimethylsilyloxy-(20S)-20-[(4-phenylpiperidin-1-yl)methyl]-5α-pregna-5-ene in 10 ml ethanol was added and the mixture was stirred 4 days at room temperature. Dichloromethane was added and the organic phase washed with sodium bicarbonate solution, dried over magnesium sulfate and concentrated under reduced pressure to give the title compound.

MS (El+): 478 (M).

EXAMPLES 17–22

Procedures d) and e) from Example 16 were repeated on 3β-tert-butyldimethylsilyloxy-(20S)-20-methyl-5α-pregna-5-en-21-al to give the following examples:

Ex. 17

(20S)-20-[(piperidin-1-yl)methyl]-5α-pregna-5-en-3β-ol (Compound No. 23)

Using piperidine in the reductive amination step d) followed by acid deprotection step e) gave the title compound.

MS (El+): 400 (M).

Ex. 18

(20S)-20-[(morpholin-4-yl)methyl]-5α-pregna-5-en-3β-ol (Compound No. 24)

Using morpholine in the reductive amination step d) followed by silyl deprotection step e) gave the title compound.

MS (El+): 402 (M).

Ex. 19

(20S)-20-[(pyrrolidin-1-yl)methyl]-5α-pregna-5-en-3β-ol (Compound No. 25)

Using pyrrolidine in the reductive amination step d) followed by silyl deprotection step e) gave the title compound.

MS (El+): 386 (M).

Ex. 20

(20S)-20-[(4-carboxyethylpiperidin-1-yl)methyl]-5α-pregna-5-en-3β-ol (Compound No. 26)

Using 4-carboxyethylpiperidine in the reductive amination step d) followed by silyl deprotection step e) gave the title compound.

MS (El+): 472 (M).

Ex. 21

(20S)-20-[(3-hydroxypiperidin-1-yl)methyl]-5α-pregna-5-en-3β-ol (Compound No. 27)

Using 3-hydroxypiperidine in the reductive amination step d) followed by silyl deprotection step e) gave the title compound.

MS (El+): 416 (M).

Ex. 22

(20S)-20-[(4-benzoylpiperidin-1-yl)methyl]-5α-pregna-5-en-3β-ol (Compound No. 28)

Using 4-benzoylpiperidine in the reductive amination step d) followed by silyl deprotection step e) gave the title compound.

MS (El+): 504 (M).

EXAMPLE 23

Testing of Meiosis-Activating Substances in the Mouse Oocyte Assay

Animals

Oocytes were obtained from immature female mice (C57Bl/6J×DBA/2J F1-hybrids, Bomholtgaard, Denmark) weighing 13–16 grams, that were kept under controlled lighting and temperature. The mice received an intraperitoneal injection of 0.2 ml gonadotropins (containing 10 IU PMSG, pregnant mare serum gonadotropin, Sigma Cat. No. G-4877) and 48 hours later the animals were killed by cervical dislocation.

Collection and Culture of Oocytes

The ovaries were dissected out and the oocytes were isolated in Hx-medium (see below) under a stereo microscope by manual rupture of the follicles using a pair of 27 gauge needles. Spherical, cumulus enclosed oocytes (CEO) displaying an intact germinal vesicle (GV) were placed in α-minimum essential medium (α-MEM without ribonucleosides, Gibco BRL, Cat. No. 22561) supplemented with 3 mM hypoxanthine (Sigma Cat. No. H-9377), 8 mg/ml Human Serum Albumin (HSA, State Serum Institute, Denmark), 0,23 mM pyruvate (Sigma, Cat. No. S-8636), 2 mM glutamine (Flow Cat. No. 16-801), 100 IU/ml penicillin and 100 μg/ml streptomycin (Flow Cat No. 16-700). This medium was designated Hx-medium.

The oocytes were rinsed three times in Hx-medium and cultured in 4-well multidishes (Nunclon, Denmark) in which each well contained 0.4 ml of Hx-medium and approx. 25 oocytes. One control (i.e. approx. 25 oocytes cultured in Hx-medium with no addition of test compound) was always run simultaneously with the test cultures, which were made with different concentrations of the compounds to be tested. The cultures were performed at 37° C. and 100% humidity with 5% $CO_2$ in air. The culture time was 22 hours.

Examination of Oocytes

Oocytes arrested in meiosis are characterized by an intact nucleus with a prominent nucleolus, known as germinal vesicle (GV). Upon reinitiation of meiosis the nucleolus and the nuclear envelope disappear and this is characterized by a breakdown of the GV, which than is called germinal vesicle breakdown (GVB). Some hours later the oocyte complete a reductional division and elicit the first so called polar body (PB).

By the end of the culture period, the number of oocytes with germinal vesicle (GV) or germinal vesicle breakdown (GVB) and those with polar body (PB) was counted using a stereo microscope or an inverted microscope with differential interference contrast equipment. The percentage of oocytes with GVB per total number of oocytes and the percentage of oocytes with PB per total number of oocytes was calculated in the test cultures and compared to the control culture.

TABLE 1

Activation of meiosis in cumulus enclosed mouse oocytes

| Compounds | Oocytes [n] | | | Activation [%] |
| --- | --- | --- | --- | --- |
| | GV | GVB | PB | GVB + PB |
| Control (Hx) | 19 | 1 | 4 | 21 |
| 10 μM FF-MAS | 13 | 6 | 5 | 46 |
| 0,1 μM compound Example 1 | 14 | 7 | 2 | 39 |
| 1 μM compound Example 1 | 6 | 12 | 6 | 75 |
| 10 μM compound Example 1 | 1 | 14 | 7 | 95 |

Hx = Hypoxanthine
GV = germinal vesicle
GVB = germinal vesicle breakdown
PB = polar bodies
n = number of oocytes

EXAMPLE 24

Testing of Meiosis-Activating Substances in the Mouse Follicular Culture System

Animals

Follicles were obtained from 19–21 day-old immature female mice (C57Bl/6J×CBA/J), that were kept under controlled lighting and temperature.

Collection of Serum and Culture of Follicles

Animals were anesthetized with ether, and blood was collected by means of eye extraction. After clotting, blood was centrifuged for 15 min at 4000×g, and serum was collected and stored at −20° C. until use. Ovaries were removed and placed in Leibovitz L-15 medium (Gibco Cat. No. 41300) supplemented with 1 mmol glutamine $l^{-1}$, 3 mg BSA $ml^{-1}$, 5 μg human transferrin $ml^{-1}$ (without iron), 5 μg insulin $ml^{-1}$ (culture-grade chemicals, Sigma, St. Louis, Mo.) at 37□C.

Preantral follicles with a diameter of 170–190 μm were isolated mechanically with two 27-gauge needles attached to 1 ml syringe. They were placed and washed thereafter (3 times) in 4-well culture plates (Nunclon, Denmark) in α-minimum essential medium (α-MEM; Gibco Cat. No. 11900) supplemented with 2 mmol glutamine $l^{-1}$, 10 μg transferrin $ml^{-1}$ and 10 μg insulin ml and with 3 mg BSA $ml^{-1}$.

Follicles of 170–190 μm with normal morphological appearance, i.e. a central spherical oocyte, high density of granulosa cells, and a theca layer enclosing the entire follicle, were selected and individually cultured in 96-well culture plate (Nunclon, Denmark) inserts with 40 μl α-MEM culture medium supplemented with 50 μl immature mouse serum $ml^{-1}$, 5 μg insulin $ml^{-1}$, 2 mmol glutamine $l^{-1}$, 10 μg human transferrin $ml^{-1}$ and 0.2 IU FSH (Gonal F, Serono, Solna, Sweden). Without any oil cover follicles were cultured in a humidified incubator gassed with 5% $CO_2$ in air at 37° C.

Start of culture was defined as day 0. Culture medium was exchanged every other day. The diameter of the follicles was measured each day using ×100 magnification and a calibrated micrometer. In addition, the survival rate of the follicles was checked by evaluation of degeneration (darkening of the follicle) and bursting (loss of the oocyte). The culture time was 4 days.

At day 2 and day 3 of culture test compound or vehicle at a volume of 1.72 μl was added to the culture medium. Test compounds were dissolved in ethanol (vehicle).

Examination of Follicles

Oocytes arrested in meiosis are characterized by an intact nucleus with a prominent nucleolus, known as germinal vesicle (GV). Upon reinitiation of meiosis the nucleolus and the nuclear envelope disappear and this is characterized by a breakdown of the GV, which then is called germinal vesicle breakdown (GVB).

At day 4, by the end of the culture period, follicles were checked for resumption of meiosis. The number of follicles having oocytes with germinal vesicle (GV) or germinal vesicle breakdown (GVB) was counted using a stereo microscope or an inverted microscope with differential interference contrast equipment. The percentage of follicles with GVB per total number of follicles was calculated in the test cultures and compared to the vehicle control culture.

TABLE 2

Activation of oocyte maturation in the mouse follicular culture system

| Compounds | Follicles [n] | | Activation [%] |
| --- | --- | --- | --- |
| | GV | GVB | GVB |
| Control (1,72 ethanol)) | 16 | 2 | 11 |
| 10 μM FF-MAS | 9 | 0 | 0 |
| 1 μM compound Example 1 | 2 | 7 | 78 |
| 3 μM compound Example 1 | 0 | 9 | 100 |
| 10 μM compound Example 1 | 0 | 8 | 100 |

GV = oocytes with a germinal vesicle
GVB = oocytes with germinal vesicle breakdown
n = number of follicles

EXAMPLE 25

Treatment of Infertility with the use of MAS Agonist in vitro

Eggs were retrieved by ultrasound guided transvaginal aspiration from the ovary of an either hormone stimulated or un-stimulated female patient.

The hormone stimulation could be the standard long IVF protocol comprising using down regulation with Gonatropin antagonist, e.g. Synarella nose-spray, followed after 14 days by FSH daily injection (Gonal-F given SC) 150 IU daily. 36 hours before egg collection the patient was given hCG (10.000 IU human chorion gonadotropin, SC) to induce final maturation of follicle and oocyte.

The compound was added to culture media in 3 μM concentration and allowed to interact with the gamete prior to fertilization either to mediate or to improve the process of meiotic maturation. The oocytes were fertilized in vitro, cultured in vitro and back-transferred to the patient uterus typically on day 3 after oocyte collection. The patient was given progesterone (crinone vaginal gel, 1 doser per day) and/or oestradiol (oestradiol-valerate 2 mg/day) to improve implantation and render the uterus more receptive.

The compound added to culture medium significantly improved on the quality of oocyte maturation, which led to higher fertilization rates, higher pre-implantation development, higher implantation rates and ultimately a higher success rate of healthy born human infants.

EXAMPLE 26

Treatment of Female Infertility with the Use of MAS Agonist in vivo

The compound was administered orally twice per day in a dose of 10 mg/kg to the female patient from the day at the time of final oocyte maturation induced by injection of hCG (10.000 IU human chorion gonadotropin, SC). The hCG could be given in a normal cycle. The cycle could be induced by withdrawal of progesterone administered minimum 10 days prior to withdrawal to induce bleeding and cyclic activity in the patient with amenorrhoea or PCO☐s (polycystic ovarian syndrome). OR the hCG could be given as an integrated part of normal long-hormone stimulation in an IVF protocol (using down regulation with Gonadotropin antagonist, e.g. Synarella nose-spray followed after 14 days by FSH daily injection of 150–225 IU daily.

The patient received the treatment either as an add-on to normal IVF treatment with egg collection, IVF and embryo transfer. Or alternatively the treatment was used in combination with fertilization obtained using insemination or natural intercourse.

The treatment elevated the patient's serum level of MAS agonists immediately close to ovulation whereby an improved oocyte maturation quality was obtained. The ovulated egg quality was improved by the meiosis induction of the daily administrated compound, which led to higher fertilization rates, higher pre-implantation development, higher implantation rates and ultimately a higher success rate of healthy born human infants.

EXAMPLE 27

Treatment of Male Infertility with the Use of MAS Agonist in vivo

The compound was administered orally twice per day in a dose of 10 mg/kg to the male patient consecutive for at least 60 (sixty) days.

The treatment elevated the patient's serum level of MAS agonists, which positively stimulated the processes of meiosis in the testis and consequently over time the semen quality parameters. The patient's semen quality parameters (number of spermatozoa, morphology, progressive motility etc) individually or altogether was improved leading to improved fertility of said person☐s semen.

This had the effect that ICSI fertilization could be avoided and only IVF fertilization could be obtained or in another example that IVF/ICSI fertilization was avoided and fertilization by insemination or natural conception could be obtained.

EXAMPLE 28

Treatment Regimen for Female Contraception Using MAS Agonist and Premature Oocyte Maturation The compound was administered orally twice per day in a dose of 50 mg/kg to the female patient every day throughout the normal cycle. The patient received the treatment either as an add-on to normal IVF treatment with egg collection, IVF and embryo transfer. Or alternatively the treatment was used in combination with fertilization obtained using insemination or natural intercourse.

The treatment elevated the patient's serum level of MAS agonists long before ovulation occurred and mediated oocyte maturation long before ovulation. When ovulated, the resulting overmature oocytes were no longer viable or able to be fertilized. The normal menstrual cycle was not to be affected, nor was the normal level and dynamics of steroid hormones altered.

EXAMPLE 29

Treatment Regimen for Female Contraception Using a MAS Antagonist Blocking the Process of Meiosis in Ovaries The compound was administered orally twice per day in a dose of 50 mg/kg to the female individual every day throughout the normal cycle.

The treatment elevated the subject's serum level of MAS antagonists, which effectively inhibited the natural oocyte maturation to occur. The process of ovulation occurred normally and the cyclic activity remained unaltered. However, at the time of ovulation a meiosis arrested and thus immature and unfertilizable oocyte were ovulated. The normal levels and dynamics of steroid hormones remained unaffected as well as the natural cyclic activity and monthly menses remained unaffected.

EXAMPLE 30

Treatment Regimen for Male Contraception Using a MAS Antagonist Blocking the Process of Meiosis in Testis The compound was administered orally twice per day in a dose of 50 mg/kg to the male individual every day consecutively for a minimum of 60 days. The process of spermatogenesis took approximately 60–65 days in the human male.

The treatment induced a level of MAS antagonists in the treated subject's serum, which effectively inhibited the natural meiotic process and specialization that led to the formation of fertilizing mature spermatozoa in the subject's testis. The process of spermatogenesis was inhibited and exclusively non-fertilizing spermatozoa were produced and released. However, the endocrinology of the testis was unaffected and the normal levels and dynamics of steroid hormones remained unaltered.

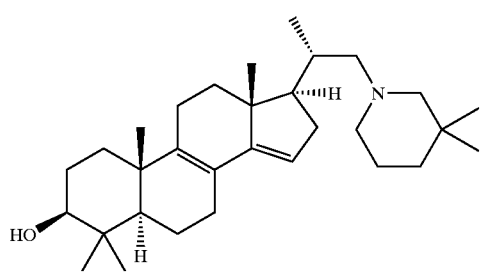

FIG. 1A

-continued

2

3

4

5

6

-continued

7

8

9

10

11

12
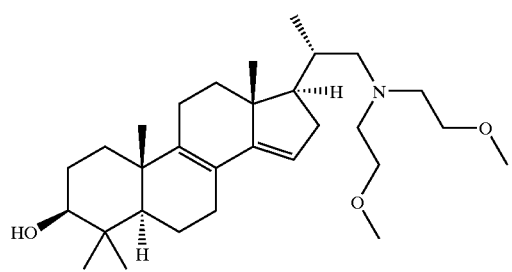
17
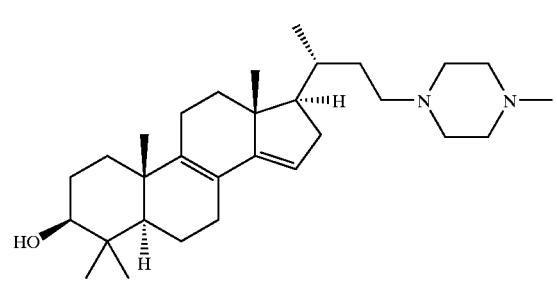
13
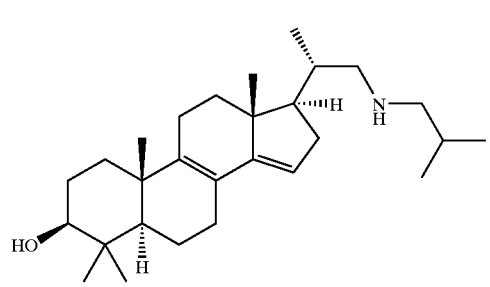
18
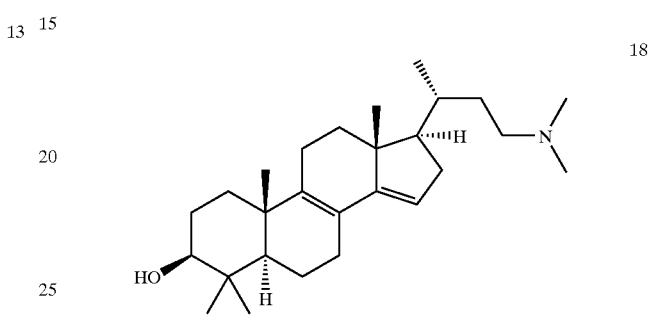
14
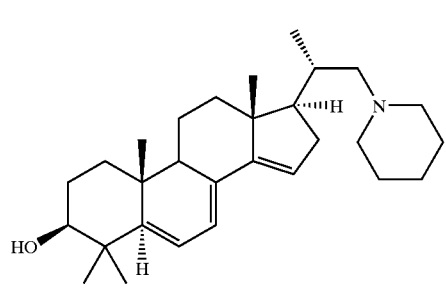
19
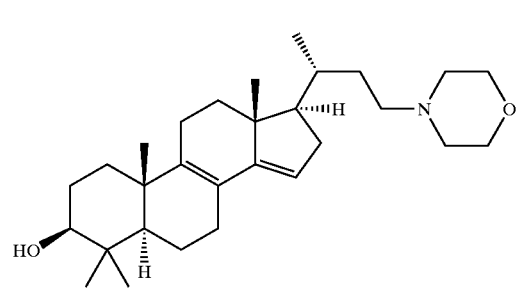
15
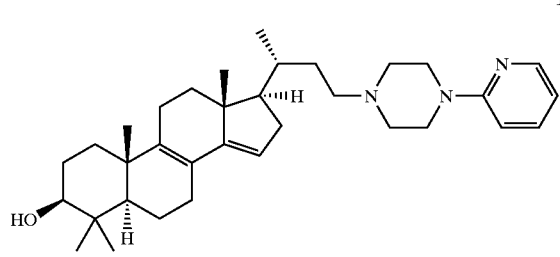
20
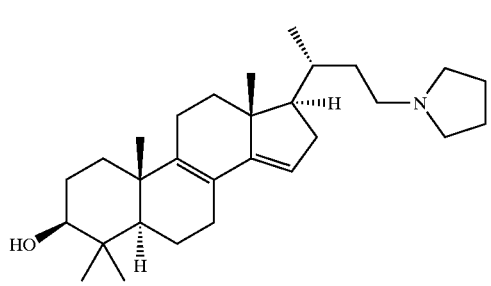
FIG. 1D
16
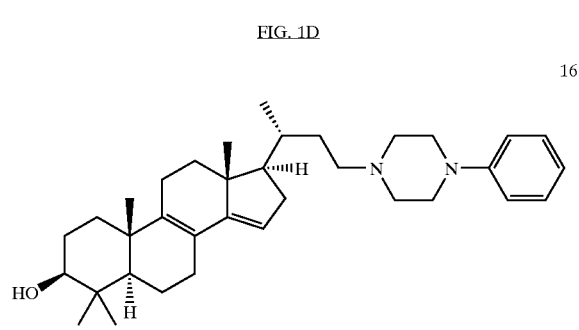
21
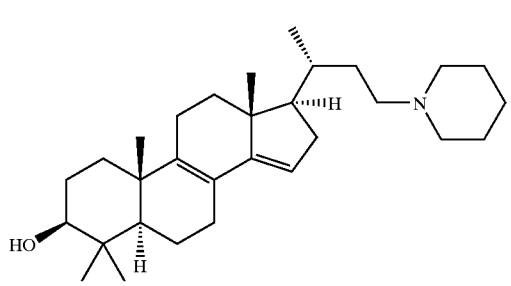

FIG. 2
Scheme 1

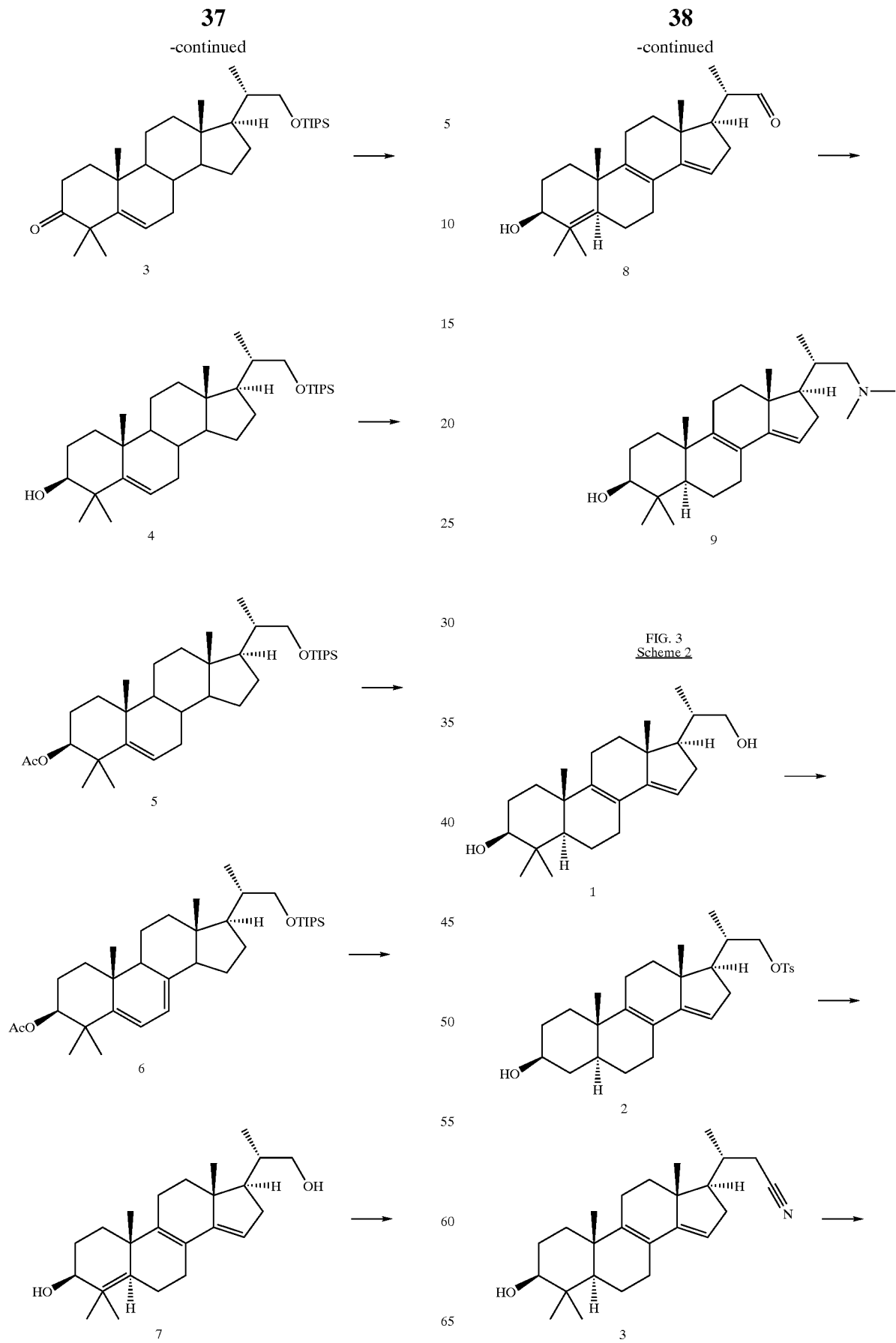

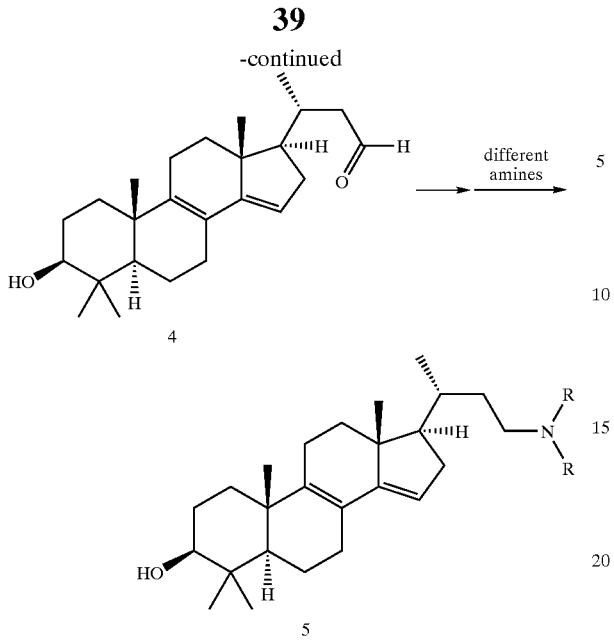

The preceding examples can be repeated with similar success by substituting the generically or specifically described reactants and/or operating conditions of this invention for those used in the preceding examples.

The entire disclosures of all applications, patents and publications, cited above or below, and of corresponding European application No. 01250108.6, filed Mar. 26, 2001, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A steroid compound of formula X

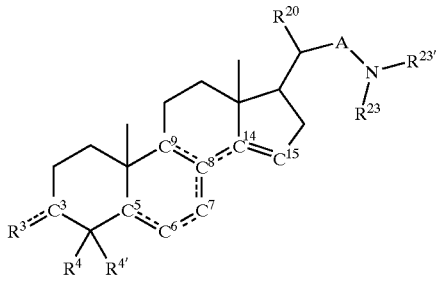

wherein in moiety XA of compound X

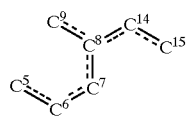

double bonds are present in the 8 and/or 14 positions, wherein:

$C^3R^3$ is a) C=O b) CH—$OR^{3'}$, wherein $R^{3'}$ is hydrogen, unsubstituted or substituted, linear or branched $C_1$–$C_{10}$ alkyl or —C(O)—$R^{3''}$, bonded to the CH—O moiety via the C(O) moiety, wherein $R^{3''}$ is i) substituted or unsubstituted, linear or branched $C_1$–$C_{10}$ alkyl,
ii) substituted or unsubstituted, linear or branched $C_1$–$C_{10}$ fluoro alkyl,
iii) unsubstituted or substituted $C_6$–$C_{10}$ aryl,
iv) unsubstituted or substituted $C_5$–$C_{10}$ heteroaryl,
v) unsubstituted or substituted, linear or branched $C_1$–$C_{10}$ alkyloxy or
vi) unsubstituted or substituted, linear or branched $C_1$–$C_{10}$ alkylamino, c) CH—$SO_2$—$R^{3''}$ or C=$NOR^{3''}$, wherein $R^{3''}$ has the same meaning as above, or d) CH—O—$R^{3'''}$ wherein $R^{3'''}$ is unsubstituted or substituted, linear or branched $C_2$–$C_{10}$ alkylene and forms a cyclic ether both with the $C^3$ atom of the steroid skeleton and the O atom, e) a cyclic ring structure with the $C^3$ atom, wherein $R^3$ is unsubstituted or substituted, linear or branched $C_2$–$C_{10}$ alkylene, or f) CH-Hal, wherein Hal is F, Cl, Br or I, and $R^4$, $R^{4'}$ and $R^{20}$, independently are hydrogen or unsubstituted or substituted, linear or branched $C_1$–$C_4$ alkyl, and $R^{23}$ and $R^{23'}$ together form a) unsubstituted or substituted, linear or branched $C_2$–$C_7$ alkylene group, or
b) unsubstituted or substituted, linear or branched $C_2$–$C_7$ alkylene group, at least one of the alkylene carbon atoms is replaced by O, N or S, and A is an unsubstituted or substituted methylene or ethylene group.

2. A steroid compound according to claim 1, wherein the double bonds in XA are conjugated.

3. A steroid compound according to claim 1, wherein XA is

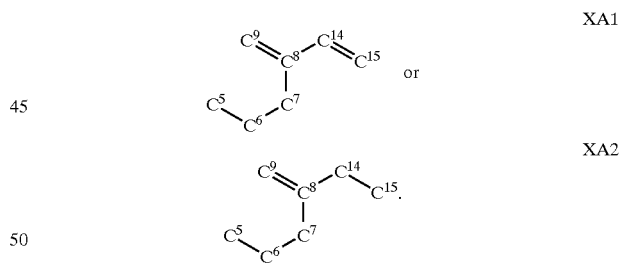

4. A steroid compound according to claim 1, wherein $C^3R^3$ is CH—OH or CH—O—C(O)—$R^{3''}$, $R^3$ is an ester radical of a monocarboxylic acid, of a dicarboxylic acid or of an inorganic acid, and/or $R^{3''}$ is $(CH_2)_n$—COOH, wherein n=1, 2, 3, 4, 5 or 6, or fluoromethyl.

5. A steroid compound according to claim 1, wherein $R^{3'}$ is acetyl, propionyl, pivaloyl, butanoyl, benzoyl, nicotinyl, isonicotinyl, hemi succinoyl or hemi glutaroyl.

6. A steroid compound according to claim 1, wherein $R^4$ and $R^{4'}$, independently, are hydrogen, or $C_1$–$C_4$ alkyl, substituted by halogen, hydroxy, alkyloxy or aryloxy.

7. A steroid compound according to claim 1, wherein $R^{20}$ is hydrogen or methyl.

8. A steroid compound according to claim 1, wherein $R^{23}$ and $R^{23'}$ together with the ammo nitrogen form a nitrogen containing heterocyclic ring which is piperidin-1-yl, morpholin-4-yl, piperazin-1-yl, pyrrolidin-1-yl, pyrrol-1-yl, indol-1-yl, pyrazol-1-yl, imidazol-1-yl, thiazolidin-1-yl, or oxazolidin-3-yl or a substituted derivative thereof.

9. A steroid compound according to claim 8, wherein the heterocyclic ring is substituted with an alkyl, alkenyl, alkynyl, cycloalkyl, cycloalkenyl, alkylcycloalkyl, aryl, alkylaryl, hydroxy, alkoxy, alkylcycloalkyloxy, alkyloxycycloalkyl, alkylaryloxy, alkyloxyaryl, halogen or acyl.

10. A steroid compound according to claim 1, wherein A is ethylene.

11. A steroid compound according to claim 1, wherein XA is

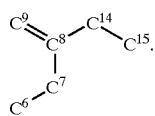

12. A steroid compound according to claim 1, wherein $C^3R^3$ is CH—OH or CH—O—C(O)—$R^{3"}$.

13. A steroid compound according to claim 1, wherein $R^3$ is an ester radical of a monocarboxylic acid, a dicarboxylic acid or of an inorganic acid.

14. A steroid compound according to claim 1, wherein $R^{3"}$ is $(CH_2)_n$—COOH, wherein n=1, 2, 3, 4, 5 or 6.

15. A steroid compound according to claim 1, wherein $R^{3"}$ is fluoromethyl.

16. A steroid compound according to claim 1, wherein $R^4$ and $R^{4'}$, independently, are hydrogen or methyl.

17. A steroid compound according to claim 1, wherein $R^4$ and $R^{4'}$, independently, are $C_1$–$C_4$ alkyl, substituted by halogen, hydroxy, alkyloxy or aryloxy.

18. A steroid compound according to claim 1, wherein $R^{20}$ is hydrogen.

19. A steroid compound according to claim 1, wherein $R^{23}$ and $R^{23'}$ together with the amino nitrogen form a nitrogen containing heterocyclic ring which is piperidin-1-yl, morpholin-4-yl, piperazin-1-yl, pyrrolidin-1-yl, pyridin-1-yl, chinolin-1-yl, isochinolin-1-yl, pyridazin-1-yl, pyrimidin-1-yl, pyrazin-1-yl, pyrrol-1-yl, indol-1-yl, chinoxalin-1-yl, pyrazol-1-yl, imidazol-1-yl, thiazol-1-yl or oxazol-3-yl or a substituted derivative thereof.

20. A steroid compound according to claim 1, wherein $R^{23}$ and $R_{23'}$ together with the amino nitrogen form a nitrogen containing heterocyclic ring which is piperidin-1-yl, morpholin-4-yl, piperazin-1-yl and pyrrolidin-1-yl.

21. A steroid compound according to claim 19, wherein the ring is substituted with an alkyl, alkenyl, alkynyl, cycloalkyl, cycloalkenyl, alkylcycloalkyl, aryl, alkylaryl, hydroxy, alkoxy, alkylcycloalkyloxy, alkyloxycycloalkyl, alkylaryloxy, alkyloxyaryl, halogen or acyl.

22. A steroid compound according to claim 10, wherein A is methylene.

23. A steroid compound according to claim 1, which is
(20S)-20-[(3,3-dimethylpiperidin-1-yl)methyl]-4,4-dimethyl-5α-pregna-8,14-dien-3β-ol,
(20S)-20-[(piperidin-1-yl)methyl]-4,4-dimethyl-5α-pregna-8,14-dien-3β-ol,
(20S)-20-[(4,4-dimethylpiperidin-1-yl)methyl]-4,4-dimethyl-5α-pregna-8,14-dien-3β-ol,
(20S)-20-[(4-methylpiperazin-1-yl)methyl]-4,4-dimethyl-5α-pregna-8,14-dien-3β-ol,
(20S)-20-[(4-phenylpiperazin-1-yl)methyl]-4,4-dimethyl-5α-pregna-8,14-dien-3β-ol,
(20S)-20-[(morpholin-4-yl)methyl]-4,4-dimethyl-5α-pregna-8,14-dien-3β-ol,
(20S)-20-[(4-(pyrimidin-2-yl)piperazin-1-yl)methyl]-4,4-dimethyl-5α-pregna-8,14-dien-3β-ol,
(20S)-20-[(pyrrolidin-1-yl)methyl]-4,4-dimethyl-5α-pregna-8,14-dien-3β-ol,
(20S)-20-[(3,3-dimethylpiperidin-1-yl)methyl]-4,4-dimethyl-5α-pregna-8,14-dien-3β-ol hemisuccinate,
(20S)-20-[(4-(pyridin-2-yl)piperazin-1-yl)ethyl]-4,4-dimethyl-5α-pregna-8,14-dien-3β-ol,
(20S)-20-[(4-phenylpiperazin-1-yl)ethyl]-4,4-dimethyl-5α-pregna-8,14-dien-3β-ol,
(20S)-20-[(4-methylpiperazin-1-yl)ethyl]-4,4-dimethyl-5α-pregna-8,14-dien-3β-ol,
(20S)-20-[(morpholin-4-yl)ethyl]-4,4-dimethyl-5α-pregna-8,14-dien-3β-ol,
(20S)-20-[(pyrrolidin-1-yl)ethyl]-4,4-dimethyl-5α-pregna-8,14-dien-3β-ol or
(20S)-20-[(piperidin-1-yl)ethyl]-4,4-dimethyl-5α-pregna-8,14-dien-3β-ol.

24. A pharmaceutical composition comprising a steroid compound of claim 1 and a pharmaceutically acceptable excipient.

25. A method of regulating reproduction, comprising administering to a patient in need thereof an effective amount of a compound of claim 1.

26. A method of regulating meiosis, comprising administering to a patient in need thereof an effective amount of a compound of claim 1.

27. A method for improving the chance of an oocyte's ability to develop into a mammal, comprising contacting an oocyte removed from the mammal with a compound of claim 1.

28. A method of preparing a compound of claim 1, wherein $R^4$ and $R^{4'}$ are unsubstituted or substituted, linear or branched $C_1$–$C_4$ alkyl, comprising
substituting a (20S)-20-methyl-pregna-8,14-dien-3β,21-diol at $C^{21}$ with cyanide, reducing the resultant nitrile to form an aldehyde, and reductively aminating the aldehyde to form an amine.

29. A method according to claim 28, wherein the substitution at $C^{21}$ is achieved by nucleophilic attack.

30. A method of preparing a compound of claim 1, wherein $R^4$ and $R^{4'}$ are unsubstituted or substituted, linear or branched $C_1$–$C_4$ alkyl, comprising
alkylating (20S)-20-hydroxymethyl-pregna-4-en-3-one to introduce two alkyl groups in position 4,
reducing the keto group of the resultant compound to a hydroxy group,
introducing a $\Delta^7$ double bond by bromination/dehydrobromination into the resultant compound,
isomerizing the resultant dien $\Delta^{5,7}$ to a dien $\Delta^{8,14}$ by heating in the presence of an acid,
oxidizing the 17-hydroxy group of the resultant compound to an aldehyde group and reductively aminating the aldehyde group.

31. A steroid compound according to claim 23, which is (20S)-20-[(piperidin-1-yl)methyl]-4,4-dimethyl-5α-pregna-8,14-dien-3β-ol.

32. A pharmaceutical composition comprising a steroid compound of claim 31 and a pharmaceutically acceptable excipient.

33. A method of regulating reproduction, comprising administering to a patient in need thereof an effective amount of a compound of claim 31.

34. A method of regulating meiosis, comprising administering to a patient in need thereof an effective amount of a compound of claim 31.

35. A method for improving the chance of an oocyte's ability to develop into a mammal, comprising contacting an oocyte removed from the mammal with a compound of claim 31.

36. A method of preparing a steroid compound according to claim 31, comprising alkylating (20S)-20-hydroxymethyl-pregna-4-en-3-one to introduce two alkyl groups in position 4, reducing the keto group of the resultant compound to a hydroxy group, introducing a $\Delta^7$ double bond by bromination/dehydrobromination into the resultant compound, isomerizing the resultant dien $\Delta^{5,7}$ to a dien $\Delta^{8,14}$ by heating in the presence of an acid, oxidizing the 17-hydroxy group of the resultant compound to an aldehyde group and reductively aminating the aldehyde group.

* * * * *